United States Patent
Nahavandi et al.

(10) Patent No.: US 11,723,823 B2
(45) Date of Patent: Aug. 15, 2023

(54) MULTI-FUNCTION HEADBOARD FOR PATIENT SUPPORT APPARATUS

(71) Applicant: Stryker Corporation, Kalamazoo, MI (US)

(72) Inventors: Kurosh Nahavandi, Portage, MI (US); Charles Louis Crouch, Plainwell, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 17/831,477

(22) Filed: Jun. 3, 2022

(65) Prior Publication Data
US 2022/0287898 A1      Sep. 15, 2022

Related U.S. Application Data

(63) Continuation of application No. 16/204,148, filed on Nov. 29, 2018, now Pat. No. 11,389,354.
(Continued)

(51) Int. Cl.
*A61G 7/00*      (2006.01)
*A61G 7/05*      (2006.01)
(Continued)

(52) U.S. Cl.
CPC ........... *A61G 7/0506* (2013.01); *A61G 12/00* (2013.01); *A61M 21/02* (2013.01); *A61G 7/015* (2013.01);
(Continued)

(58) Field of Classification Search
CPC ...... A61G 7/0506; A61G 12/00; A61G 7/015; A61G 2203/12; A61G 7/00; A61M 21/02;
(Continued)

(56) References Cited

U.S. PATENT DOCUMENTS

| | | | |
|---|---|---|---|
| 4,811,435 A | | 3/1989 | Foster et al. |
| 5,542,138 A | * | 8/1996 | Williams ............... F16M 11/14 5/503.1 |

(Continued)

FOREIGN PATENT DOCUMENTS

WO      2012135118 A1      10/2012

OTHER PUBLICATIONS

Hill-Rom, "Centrella Smart+Bed Brochure" 2017, 11 pages.
Stryker, "Maintenance Manual for InTouch Critical Care Bed Model FL27", Version 3, Jun. 2012, 5 pages.

*Primary Examiner* — Fredrick C Conley
(74) *Attorney, Agent, or Firm* — Howard & Howard Attorneys PLLC

(57) ABSTRACT

A patient support apparatus comprises a support structure, an articulation system, and a headboard assembly. The support structure comprises a head end, a foot end, a base, and a patient support deck to support a patient between the head end and the foot end. The patient support deck comprises a first section and a second section capable of articulating relative to the first section. The articulation system articulates the second section relative to the first section. The headboard assembly is coupled to the second section to be arranged adjacent to a head of the patient lying on the patient support deck. At least a portion of the headboard assembly articulates with the second section when the second section articulates relative to the first section. The headboard assembly comprises one or more environment controls operable to alter an environment of the patient on the patient support deck.

19 Claims, 19 Drawing Sheets

Related U.S. Application Data

(60) Provisional application No. 62/592,946, filed on Nov. 30, 2017.

(51) Int. Cl.
  *A61M 21/02* (2006.01)
  *A61G 12/00* (2006.01)
  *A61G 7/015* (2006.01)
  *A61M 21/00* (2006.01)

(52) U.S. Cl.
  CPC ...... *A61G 2203/10* (2013.01); *A61G 2203/12* (2013.01); *A61G 2203/70* (2013.01); *A61M 2021/0027* (2013.01); *A61M 2021/0044* (2013.01); *A61M 2021/0066* (2013.01); *A61M 2205/07* (2013.01); *A61M 2205/3673* (2013.01); *A61M 2205/502* (2013.01); *A61M 2205/587* (2013.01); *A61M 2209/082* (2013.01)

(58) Field of Classification Search
  CPC ....... A61M 2205/502; A61M 2209/082; F24F 11/50
  See application file for complete search history.

(56) References Cited

U.S. PATENT DOCUMENTS

| | | | |
|---|---|---|---|
| 7,325,265 B2 | 2/2008 | Hornbach et al. |
| 7,543,583 B2 | 6/2009 | Acton |
| 7,636,966 B2 | 12/2009 | Gallant et al. |
| 7,766,289 B2 | 8/2010 | Newkirk et al. |
| 8,143,846 B2 | 3/2012 | Herman et al. |
| 8,151,387 B2 | 4/2012 | Osborne et al. |
| 8,418,291 B2 | 4/2013 | Hornbach et al. |
| 8,618,918 B2 | 12/2013 | Tallent et al. |
| 8,806,682 B2 | 8/2014 | Hornbach et al. |
| 9,253,259 B2 | 2/2016 | Tallent et al. |
| 9,295,390 B2 | 3/2016 | Receveur et al. |
| 9,492,340 B2 | 11/2016 | Hornbach et al. |
| 9,642,759 B2 | 5/2017 | Stryker et al. |
| 10,322,045 B1 | 6/2019 | Cuneo |
| 11,241,347 B2 | 2/2022 | Ribble et al. |
| 2001/0052152 A1 | 12/2001 | Soltani et al. |
| 2003/0033790 A1 | 2/2003 | Hague |
| 2003/0061664 A1 | 4/2003 | Salvatini et al. |
| 2005/0138727 A1 | 6/2005 | Faux et al. |
| 2006/0021145 A1* | 2/2006 | Hornbach .............. A61G 7/015 5/618 |
| 2006/0053554 A1 | 3/2006 | Acton |
| 2007/0010719 A1 | 1/2007 | Huster et al. |
| 2008/0235872 A1 | 10/2008 | Newkirk et al. |
| 2008/0263771 A1 | 10/2008 | Hakamiun et al. |
| 2009/0064415 A1 | 3/2009 | Payne et al. |
| 2009/0288253 A1 | 11/2009 | Jin |
| 2010/0005588 A1 | 1/2010 | Christopher |
| 2011/0247137 A1 | 10/2011 | Herman et al. |
| 2012/0105233 A1 | 5/2012 | Bobey et al. |
| 2012/0116591 A1 | 5/2012 | Rawls-Meehan |
| 2012/0172959 A1 | 7/2012 | Lachenbruch et al. |
| 2014/0059766 A1 | 3/2014 | Gibson et al. |
| 2015/0257952 A1 | 9/2015 | Zerhusen et al. |
| 2016/0008197 A1 | 1/2016 | Zerhusen et al. |
| 2016/0220435 A1 | 8/2016 | Stroh et al. |
| 2016/0302985 A1 | 10/2016 | Tessmer et al. |
| 2016/0367420 A1 | 12/2016 | Zerhusen et al. |
| 2017/0027789 A1 | 2/2017 | St.John et al. |
| 2017/0079434 A1 | 3/2017 | Paul et al. |
| 2017/0098048 A1 | 4/2017 | Brosnan et al. |
| 2017/0246065 A1 | 8/2017 | Connell et al. |
| 2017/0319412 A1 | 11/2017 | Herman et al. |
| 2018/0333317 A1 | 11/2018 | Zerhusen et al. |
| 2019/0167499 A1 | 6/2019 | Nahavandi et al. |

* cited by examiner

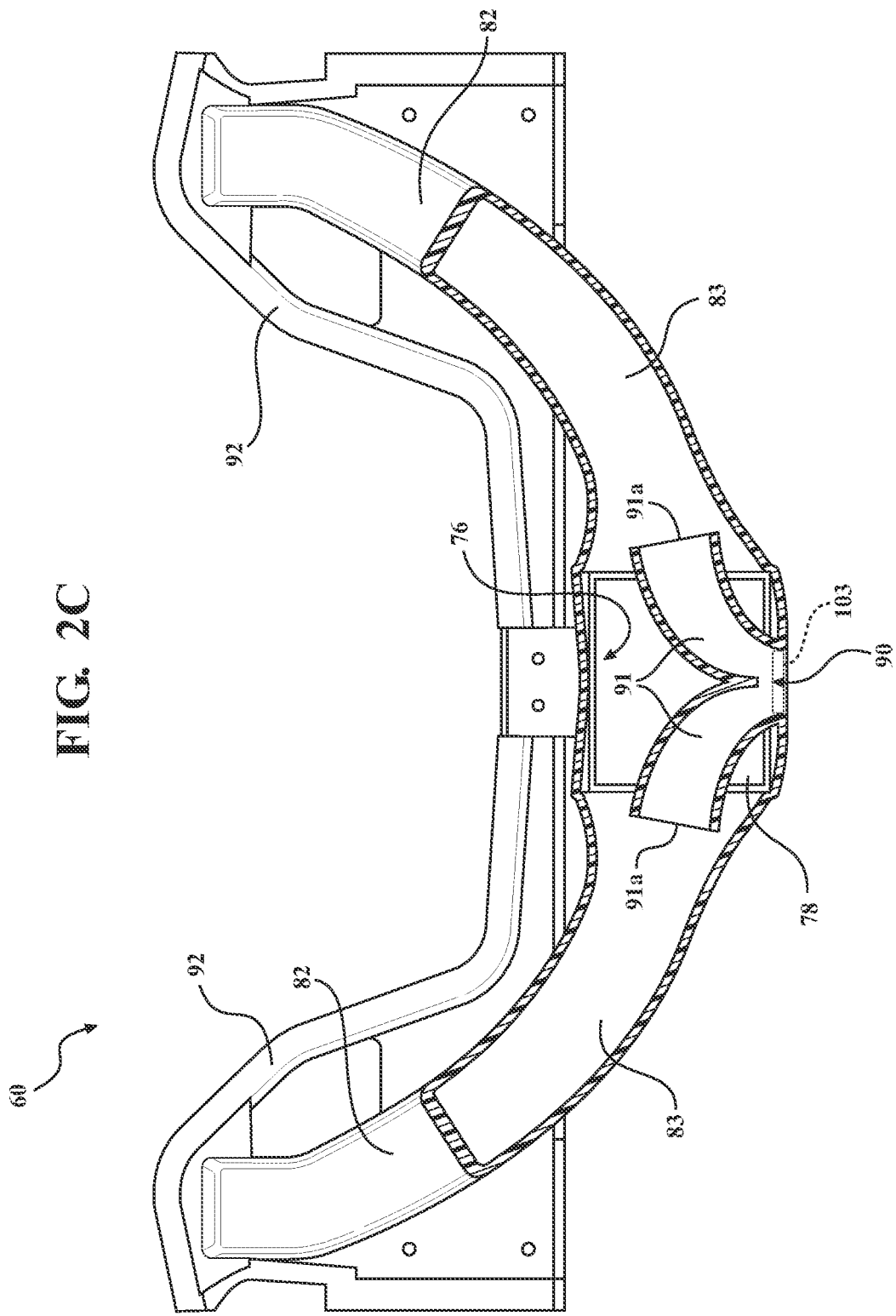

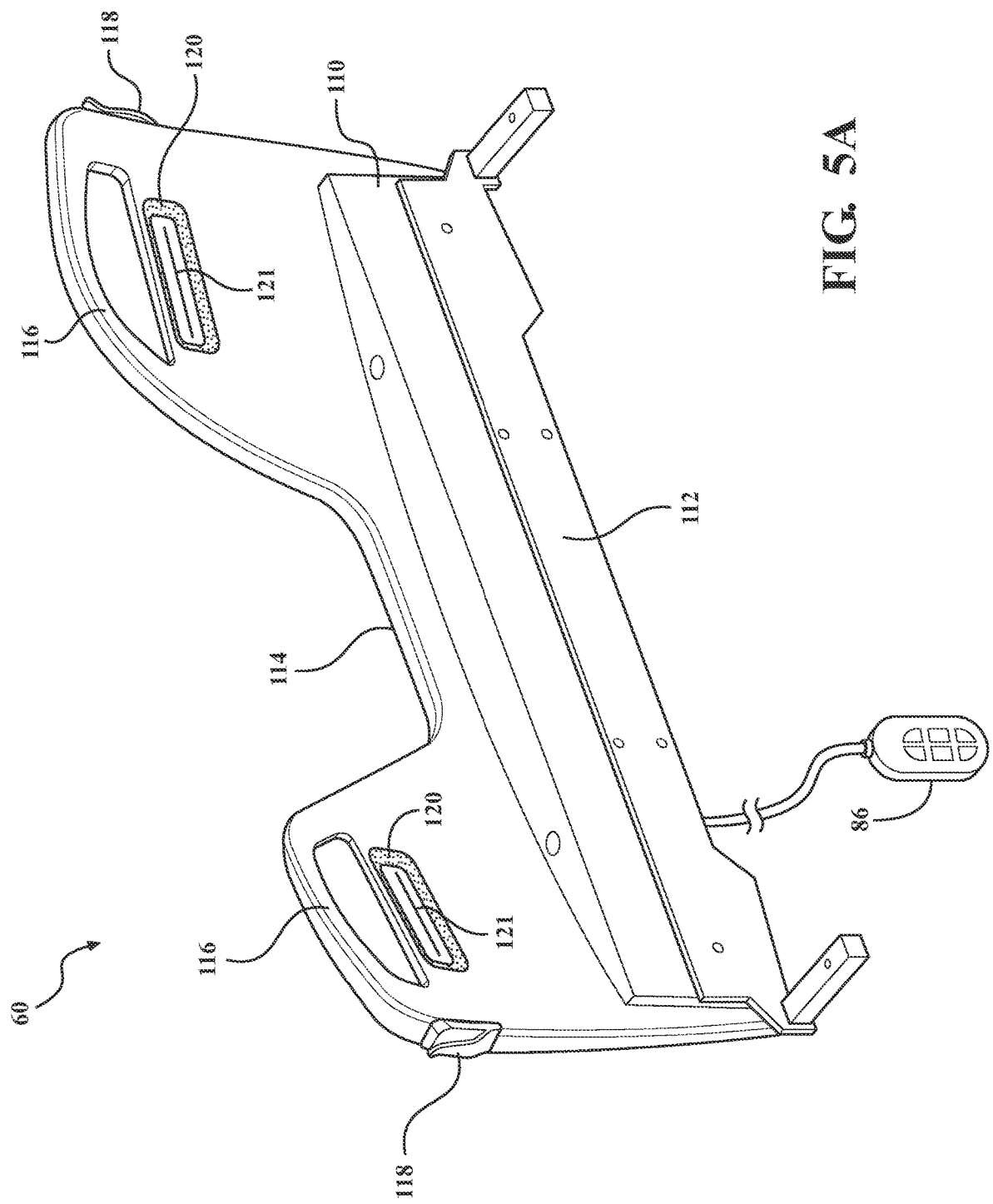

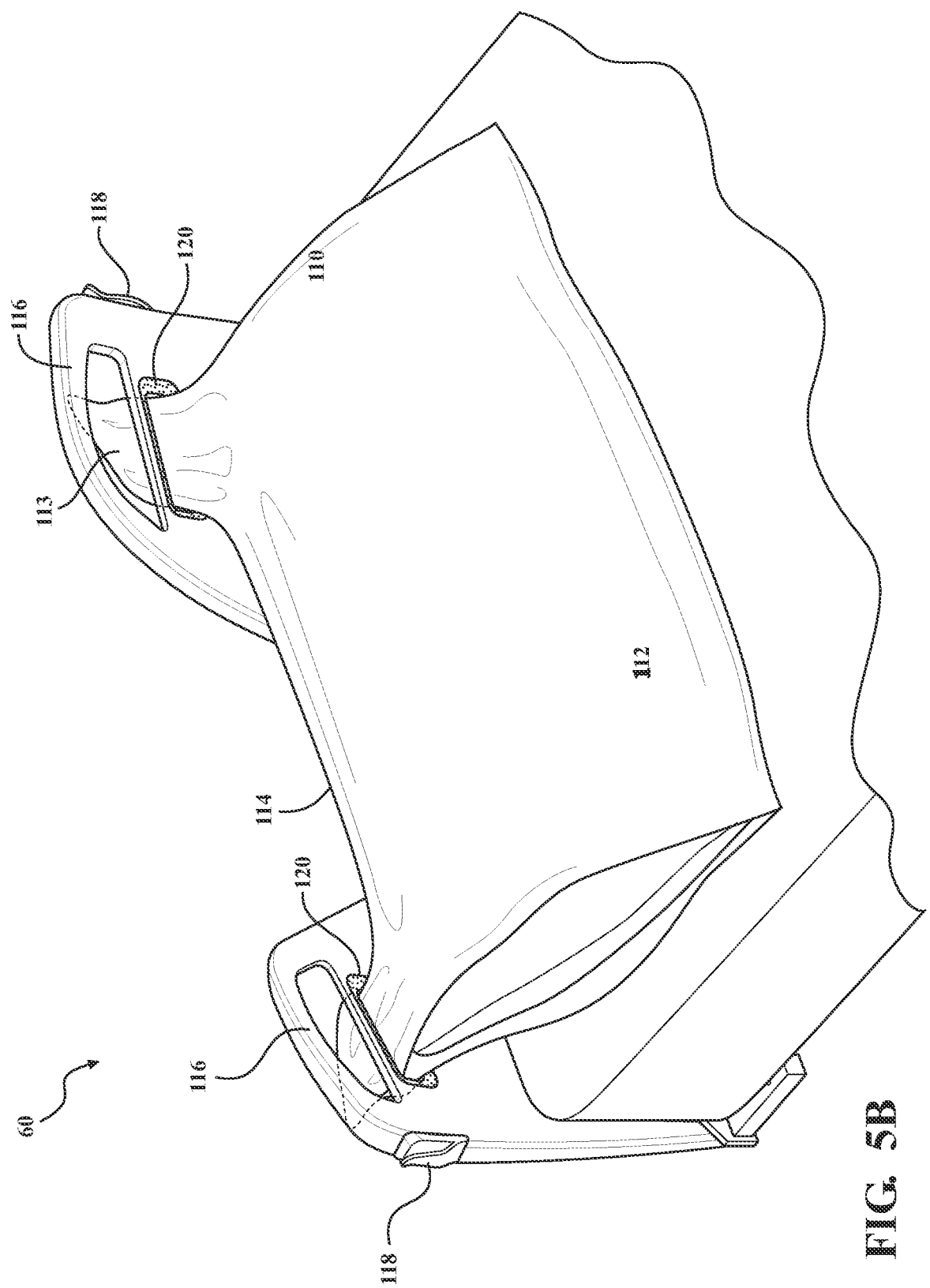

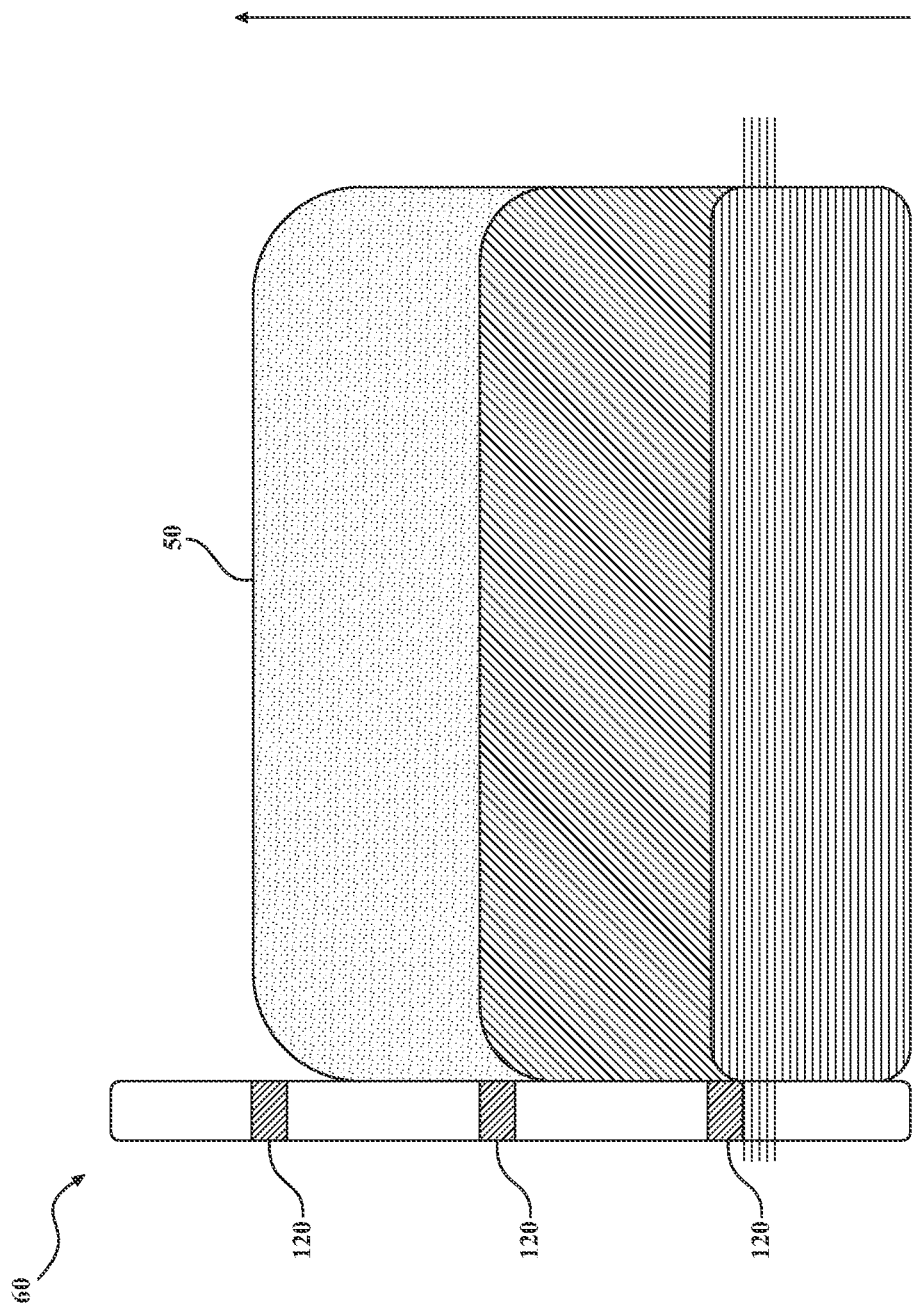

MULTI-FUNCTION HEADBOARD FOR PATIENT SUPPORT APPARATUS

RELATED APPLICATIONS

This application is a Continuation of U.S. patent application Ser. No. 16/204,148, filed on Nov. 29, 2018, which claims priority to and the benefit of U.S. Provisional Patent Application No. 62/592,946, filed on Nov. 30, 2017, the disclosures of each of which are hereby incorporated by reference in their entirety.

BACKGROUND

Patient support apparatuses, such as hospital beds, stretchers, cots, tables, wheelchairs, and chairs facilitate care of patients in a health care setting. Conventional patient support apparatuses comprise a support structure having a base, a frame, a patient support deck on the frame upon which the patient is supported, a lift system for lifting and lowering the patient support deck relative to the base, and an articulation system for articulating one or more sections of the patient support deck. The patient support apparatus may further comprise a headboard mounted to the frame, which may be removable. Often, the headboard serves only as a mattress and/or pillow barrier and can be unwieldy, and may be misplaced or discarded.

Additionally, current patient support apparatuses have no central location for housing environment controls for patient comfort, such as speakers, integrated heating/cooling systems, reading lights or nightlights, or handles for patient use. Moreover, some of these features are typically housed in side rails coupled to the frame, which usually articulate and thus are not always in an optimal position for providing sound or access to handles or other controls to the patient.

A patient support apparatus is desired that addresses one or more of the aforementioned challenges.

BRIEF DESCRIPTION OF THE DRAWINGS

FIG. 2C is a cross-sectional view of the headboard assembly according to the first embodiment.

FIG. 5A is a front perspective view of a headboard assembly of the patient support apparatus according to a third embodiment.

FIG. 5B is a front perspective view of the headboard assembly according to the third embodiment illustrating operation of retainers.

FIG. 5D is a partial side view of the headboard assembly according to the third embodiment illustrating mattresses of varying heights.

DETAILED DESCRIPTION

Figure 1A:
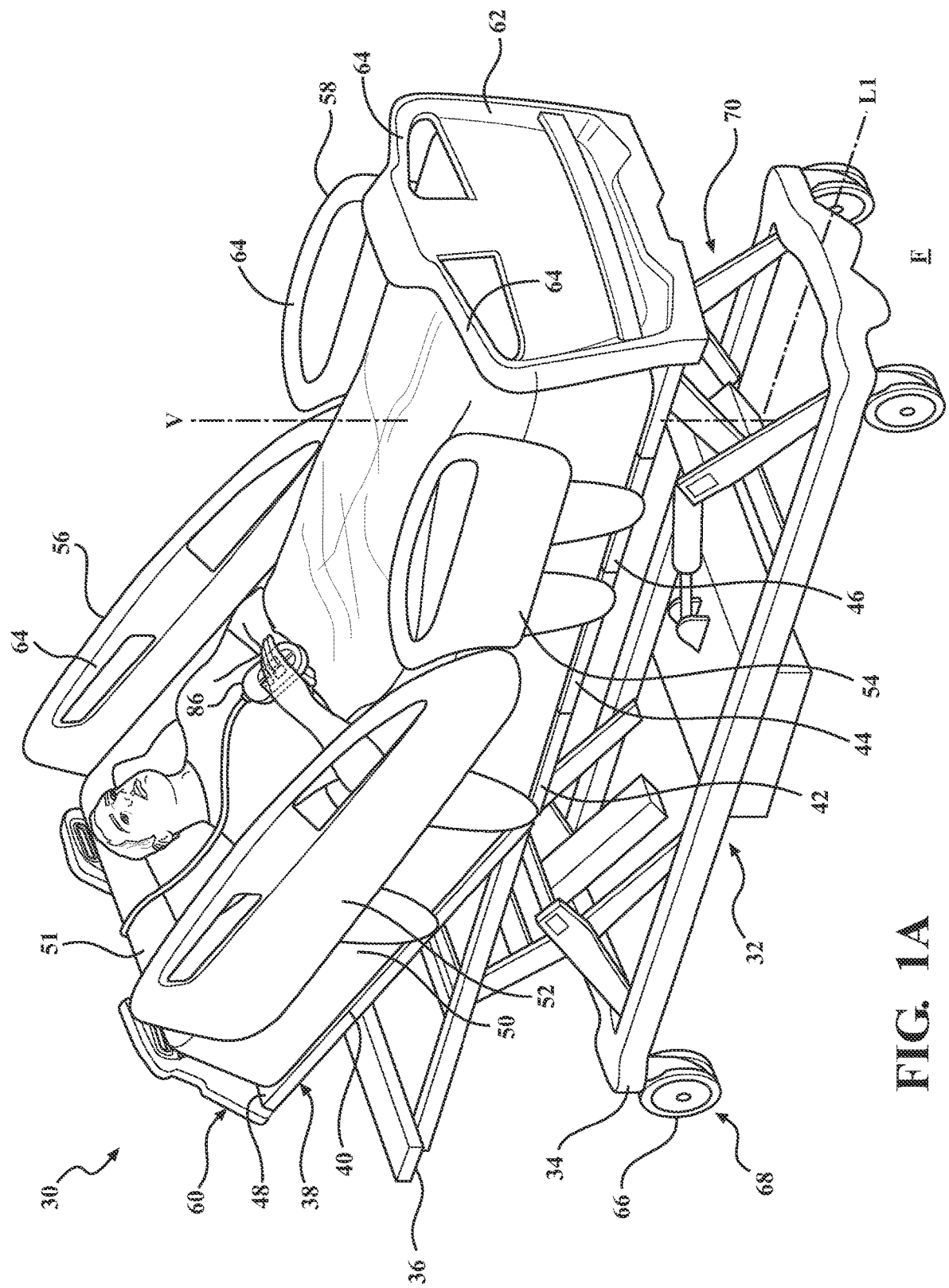
FIG. 1A is a perspective view of a patient support apparatus.

Referring to FIG. 1A, a patient support apparatus 30 is shown for supporting a patient in a health care setting. The patient support apparatus 30 illustrated in FIG. 1 comprises a hospital bed. In other embodiments, however, the patient support apparatus 30 may comprise a stretcher, cot, table, wheelchair, chair, or similar apparatus utilized in the care of a patient.

A support structure 32 provides support for the patient. The support structure 32 illustrated in FIG. 1A comprises a base 34 and a support frame 36. The support structure 32 also comprises a patient support deck 38 disposed on the support frame 36. The patient support deck 38 comprises first, second, third, and fourth sections, some of which are capable of articulating (e.g., pivoting) relative to the support frame 36, such as a fowler (back) section 40, a seat section 42, a leg section 44, and a foot section 46. The patient support deck 38 provides a patient support surface 48 upon which the patient is supported.

A mattress 50 is disposed on the patient support deck 38 during use. The mattress 50 comprises a secondary patient support surface 51 upon which the patient is supported. The base 34, support frame 36, patient support deck 38, and patient support surfaces 48, 51 each have a head end and a foot end corresponding to designated placement of the patient's head and feet on the patient support apparatus 30. The base 34 comprises a longitudinal axis L1 along its length from the head end to the foot end. The base 34 also comprises a vertical axis V arranged crosswise (e.g., perpendicularly) to the longitudinal axis L1 along which the support frame 36 is lifted and lowered relative to the base 34. The construction of the support structure 32 may take on any known or conventional design, and is not limited to that specifically set forth above. In addition, the mattress may be omitted in certain embodiments, such that the patient rests directly on the patient support surface 48.

Patient barriers, such as side rails 52, 54, 56, 58 are coupled to the support frame 36 and/or patient support deck 38 and are thereby supported by the base 34. A first side rail 52 is positioned at a right head end. A second side rail 54 is positioned at a right foot end. A third side rail 56 is positioned at a left head end. A fourth side rail 58 is positioned at a left foot end. In the embodiment shown, the head end side rails 52, 56 are mounted to the fowler section 40 for movement with the fowler section 40. The foot end side rails 54, 58 are mounted to the support frame 36 for movement with the support frame 36. If the patient support apparatus 30 is a stretcher or a cot, there may be fewer side rails. The side rails 52, 54, 56, 58 are movable relative to the fowler section 40/support frame 36 to a raised position in which they block ingress and egress into and out of the patient support apparatus 30, one or more intermediate positions, and a lowered position in which they are not an obstacle to such ingress and egress.

A headboard assembly 60 and a footboard 62 are coupled to the support frame 36. The footboard 62 may be coupled to any location on the patient support apparatus 30, such as the support frame 36 or the base 34. The headboard assembly 60 is coupled to the fowler section 40 in certain embodiments described further below, but in other embodiments may be coupled to the support frame 36, the base 34, or other suitable locations. The headboard assembly 60 is described in greater detail below.

Caregiver interfaces 64, such as handles, are shown integrated into the footboard 62, and side rails 52, 54, 56, 58 to facilitate movement of the patient support apparatus 30 over a floor surface F. Additional caregiver interfaces 64 may be integrated into other components of the patient support apparatus 30. The caregiver interfaces 64 are graspable by the caregiver to manipulate the patient support apparatus 30 for movement, to move the side rails 52, 54, 56, 58, and the like.

Other forms of the caregiver interface 64 are also contemplated. The caregiver interface may comprise one or more handles coupled to the support frame 36. The caregiver interface 64 may simply be a surface on the patient support apparatus 30 upon which the caregiver logically applies force to cause movement of the patient support apparatus 30 in one or more directions, also referred to as a push location. This may comprise one or more surfaces on the support frame 36 or base 34. This could also comprise one or more surfaces on or adjacent to the headboard assembly 60, footboard 62, and/or side rails 52, 54, 56, 58. In other embodiments, the caregiver interface may comprise separate handles for each hand of the caregiver. For example, the caregiver interface may comprise two handles.

Wheels 66 are coupled to the base 34 to facilitate transport over the floor surface F. The wheels 66 are arranged in each of four quadrants of the base 34 adjacent to corners of the base 34. In the embodiment shown, the wheels 66 are caster wheels able to rotate and swivel relative to the support structure 32 during transport. Each of the wheels 66 forms part of a caster assembly 68. Each caster assembly 68 is mounted to the base 34. It should be understood that various configurations of the caster assemblies 68 are contemplated. In addition, in some embodiments, the wheels 66 are not caster wheels and may be non-steerable, steerable, non-powered, powered, or combinations thereof. Additional wheels are also contemplated. For example, the patient support apparatus 30 may comprise four non-powered, non-steerable wheels, along with one or more powered wheels. In some cases, the patient support apparatus 30 may not include any wheels.

In other embodiments, one or more auxiliary wheels (powered or non-powered), which are movable between stowed positions and deployed positions, may be coupled to the support structure 32. In some cases, when these auxiliary wheels are located between caster assemblies 68 and contact the floor surface F in the deployed position, they cause two of the caster assemblies 68 to be lifted off the floor surface F thereby shortening a wheel base of the patient support apparatus 30. A fifth wheel may also be arranged substantially in a center of the base 34.

The patient support apparatus 30 may further comprise a lift system 70 that operates to lift and lower the support frame 36/patient support deck 38 relative to the base 34. The lift system 70 is configured to move the support frame 36/patient support deck 38 to any desired position. One exemplary lift system 70 is described below and in U.S. Patent Application Pub. No. 2017/0246065, filed on Feb. 22, 2017, entitled "Lift Assembly for Patient Support Apparatus," hereby incorporated by reference herein in its entirety. Other types of lift systems can also be used, such as those described in U.S. Patent Application Publication No. 2016/0302985, filed on Apr. 20, 2016, entitled "Patient Support Lift Assembly," hereby incorporated by reference herein in its entirety.

Figure 1B:
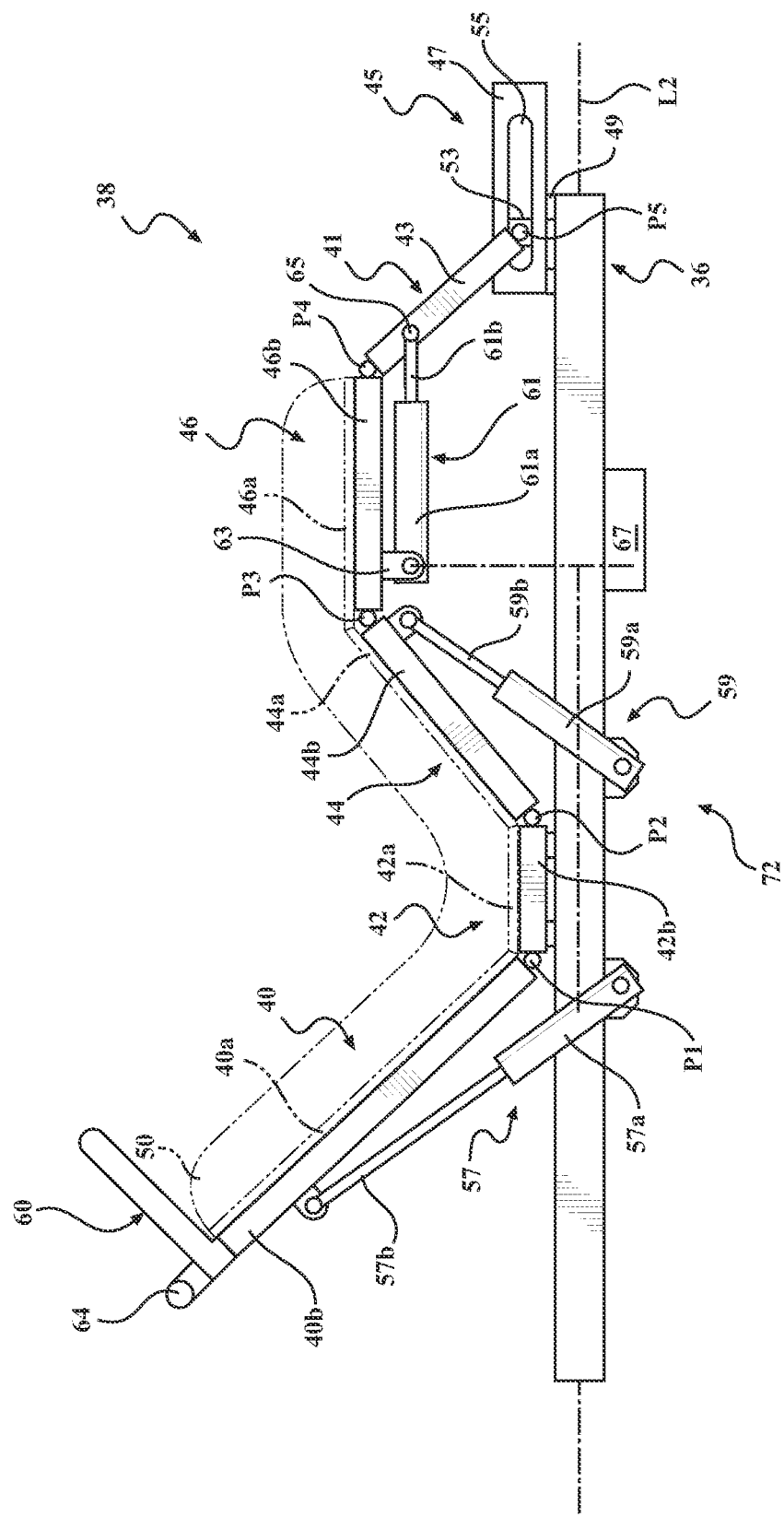
FIG. 1B is a side view of an articulation system of the patient support apparatus of FIG. 1A.

Referring to FIG. 1B, the patient support apparatus 30 may further comprise an articulation system 72 that articulates the deck sections 40, 44, and 46. Referring now to FIG. 1B, a side view of the articulation system 72 according to one embodiment is shown. In particular, the deck sections 40, 42, 44, 46 are shown in a configuration in which the fowler section 40 is raised above the support frame 36, the seat section 42 is fixed to the support frame 36 (such as by welding, fasteners, or the like), the leg section 44 is raised above the support frame 36, and the foot section 46 is elevated above the support frame 36 in a plane parallel to a second longitudinal axis L2.

The deck sections 40, 42, 44, 46 are pivotally coupled together in series at pivot joints defined about pivot axes P1, P2, P3. Each of the deck sections 40, 42, 44, 46 have a first end and a second end. The first end is closer to the head end of the patient support apparatus 30 when the patient support deck 38 is in a flat configuration and the second end is closer to the foot end of the patient support apparatus 30 when the patient support deck 38 is in the flat configuration. In the embodiment shown, the second end of the fowler section 40 is pivotally coupled to the first end of the seat section 42 about pivot axis P1. The first end of the leg section 44 is pivotally coupled to the second end of the seat section 42 about pivot axis P2. The first end of the foot section 46 is pivotally coupled to the second end of the leg section 44 about pivot axis P3.

The deck sections 40, 42, 44, 46 may be pivotally coupled together by pivot pins, shafts, and the like at the pivot joints. Pivot brackets may be employed to form the pivot joints. Additionally, other types of connections are possible between the deck sections 40, 42, 44, 46 so that the deck sections 40, 42, 44, 46 are capable of moving, e.g., articulating, relative to one another. For instance, in some cases, translational joints may be provided between adjacent deck sections, or other compound movement connections may be provided between adjacent deck sections, such as joints that allow both pivotal and translational motion between adjacent deck sections. Further, in other cases, the fowler section 40 and the leg section 44 may be pivotally (or otherwise) connected directly to the support frame 36 or other part of the support structure 32, instead of the seat section 42.

As shown by hidden lines, the deck sections 40, 42, 44, 46 comprise deck panels 40a, 42a, 44a, 46a, removably coupled to deck section frames 40b, 42b, 44b, 46b. It should be appreciated that, in other embodiments, the deck sections 40, 42, 44, 46 may comprise only the deck section frames 40b, 42b, 44b, 46b or only the deck panels 40a, 42a, 44a, 46a. The deck panels 40a, 42a, 44a, 46a may be plastic panels that snap fit or are otherwise capable of being easily removed from the deck section frames 40*b*, 42*b*, 44*b*, 46*b* for cleaning, etc. The deck panels 40*a*, 42*a*, 44*a*, 46*a*, could also be formed of other materials and may be permanently affixed to the deck sections frames 40*b*, 42*b*, 44*b*, 46*b*. Each of the deck section frames 40*b*, 42*b*, 44*b*, 46*b* may be formed of metal and comprise structural members (e.g., metal bars and tubes) welded together to form a support framework. The deck sections frames 40*b*, 42*b*, 44*b*, 46*b* could also be formed of other materials and comprise only single members, such as a single panel, frame, or other type of support structure.

A support link 41 extends between the support frame 36 and the foot section 46 to support the foot section 46. The support link 41 is arranged to support the second end of the foot section 46 with respect to the support frame 36. The support link 41 has a first link end pivotally coupled to the second end of the foot section 46. The support link 41 extends from the first link end to a second link end pivotally and slidably coupled to the support frame 36. In the embodiment shown, the support link 41 comprises a pair of spaced apart support arms 43. In other embodiments, the support link 41 may comprise only a single support arm, or other type of support member (or members) that support the second end of the foot section 46 with respect to the support frame 36.

The support arms 43 are pivotally coupled at the first link end to the foot section 46 about pivot axis P4. The support arms 43 may be pivotally coupled to the foot section 46 via pivot pins, shafts, or the like. The support arms 43 are pivotally and slidably coupled to the support frame 36 at the second link end.

The support frame 36 comprises a guide 45 that supports the second link end of the support link 41. In particular, the second link end of the support link 41 is pivotally and slidably coupled to the guide 45. Thus, the guide 45 is arranged to guide sliding movement of the second link end of the support link 41. The guide 45 comprises a pair of guide tracks 47 that are fixed to a cross frame member 49 of the support frame 36. In the embodiment shown, the guide tracks 47 are shown being formed of rectangular metal tubing. In other embodiments, the guide tracks 47 may be formed of other materials and may assume other forms or shapes capable of guiding movement of the support arms 43. In still further embodiments, a single guide track 47 may be provided. The shape of the guide tracks 47 dictate the path along which the second link end of the support link 41 follows during movement of the support link 41. In the embodiment shown in FIG. 1B, the guide tracks 47 are oriented parallel to the second longitudinal axis L2 of the support frame 36.

Guided bodies 53 are pivotally mounted to the support arms 43 about pivot axis P5 at the second link end. The guided bodies 53 are captured in the guide tracks 47 for sliding in the guide tracks 47. The guided bodies 53 are pivotally mounted to the support arms 43 via pivot pins, shafts, or the like. In the embodiment shown, pivot pins pivotally connect the support arms 43 to the guided bodies 53 through slots 55. The slots 55 are formed in one side of the guide tracks 47 and terminate at opposed ends of the guide tracks 47. The slots 55 have a shape that is at least one of linear or arcuate, or combinations thereof. The slots 55 may also comprise stepped slots, or slots of other shapes/configurations.

When the support arms 43 are pivoted, or otherwise articulated, relative to the foot section 46, the guided bodies 53 slide in the guide tracks 47, which also simultaneously causes the guided bodies 53 to pivot relative to the support arms 43. Each of the guided bodies 53 comprise one of a block, a roller, a gear, or other movable elements. In the embodiment shown, the guide tracks 47 are slide-bearing guide tracks and the guided bodies 53 comprise blocks slidable along the slide-bearing guide tracks. The blocks can be any shape, including box-shaped, spherical, cylindrical, or the like.

Actuators 57, 59, 61 operate to move the fowler section 40, leg section 44, and foot section 46. The actuators 57, 59, 61 may be linear actuators, rotary actuators, or other type of actuators capable of moving the fowler section 40, leg section 44, and foot section 46. The actuators 57, 59, 61 may be electrically powered, hydraulic, electro-hydraulic, pneumatic, or the like. In the embodiment shown, the actuators 57, 59, 61 are electrically powered linear actuators comprising actuator housings 57*a*, 59*a*, 61*a* and drive rods 57*b*, 59*b*, 61*b* that extend and retract with respect to their associated actuator housing 57*a*, 59*a*, 61*a*. Hereinafter, the actuators 57, 59, 61 shall be referred to as fowler section actuator 57, leg section actuator 59, and foot section actuator 61.

The fowler section actuator 57 is operatively connected to the fowler section 40 to pivot, or otherwise articulate, the fowler section 40 relative to the support frame 36 between a lowered position and one or more raised positions. More specifically, the fowler section actuator 57 pivots the fowler section 40 about pivot axis P1 relative to the seat section 42. In the embodiment shown, the fowler section actuator 57 is pivotally connected at a first actuator end to a mounting bracket fixed to the support frame 36. The fowler section actuator 57 is pivotally connected at a second actuator end to a mounting bracket fixed to the fowler section 40. The fowler section actuator 57 could be pivotally connected to these brackets via pivot pins, shafts, and the like. In other embodiments, the fowler section actuator 57 may be connected through other types of connections or linkages in order to move the fowler section 40 to the lowered position or the one or more raised positions.

The leg section actuator 59 is operatively connected to the leg section 44 to pivot, or otherwise articulate, the leg section 44 relative to the support frame 36 between a lowered position and one or more raised positions. More specifically, the leg section actuator 59 pivots the leg section 44 about pivot axis P2 relative to the seat section 42. Owing to the pivotal coupling of the second end of the leg section 44 to the first end of the foot section 46, when the leg section 44 is moved, the first end of the foot section 46 is also moved. In the embodiment shown, the leg section actuator 59 is pivotally connected at a first actuator end to a mounting bracket fixed to the support frame 36. The leg section actuator 59 is pivotally connected at a second actuator end to a mounting bracket fixed to the leg section 44. The leg section actuator 59 could be pivotally connected to these brackets via pivot pins, shafts, and the like. In other embodiments, the leg section actuator 59 may be connected through other types of connections or linkages in order to move the leg section 44 to the lowered position or the one or more raised positions.

The foot section actuator 61 is operatively connected to the support link 41 to move, e.g., articulate, the support link 41 relative to the foot section 46. Movement of the support link 41 causes the foot section 46 to pivot, or otherwise articulate, relative to the leg section 44 between different foot section positions. Accordingly, the foot section actuator 61 acts as a foot section adjustment device. In the embodiment shown, the foot section actuator 61 is pivotally connected at a first actuator end to a mounting bracket 63 fixed to the foot section 46. The foot section actuator 61 is pivotally connected at a second actuator end to a mounting bracket 65. The foot section actuator 61 could be pivotally connected to these brackets 63, 65 via pivot pins, shafts, and the like. In other embodiments, the foot section actuator 61 may be connected to the foot section 46 or the support link 41 through other types of connections or linkages.

During operation, when the foot section actuator 61 moves the support link 41, the second link end of the support link 41 slides relative to the guide 45. Since movement of the second link end is constrained by the guide 45, e.g., constrained to longitudinal movement or oblique movement, sliding of the second link end away from the seat section 42 causes the second end of the foot section 46 to lower relative to its first end by pivoting about pivot axis P3 (assuming leg section 44 is stationary). Sliding of the second link end toward the seat section 42 causes the second end of the foot section 46 to be raised relative to its first end by pivoting about pivot axis P3 (assuming leg section 44 is stationary).

When the foot section actuator 61 ceases operation, and the leg section actuator 59 is operated to raise or lower the leg section 44, the second link end of the support link 41 again slides with respect to the guide 45. This action is due to the foot section 46, support link 41, and the foot section actuator 61 essentially forming a single link between the second end of the leg section 44 and the guided bodies 53 because the foot section actuator 61 holds the position of the support link 41 relative to the foot section 46 when the foot section actuator 61 ceases operation.

A control system is provided to control operation of the actuators 57, 59, 61. The control system comprises a controller 67 having one or more microprocessors for processing instructions or for processing an algorithm stored in memory to control operation of the actuators 57, 59, 61 and coordinate movement of the actuators 57, 59, 61 to move one or more of the deck sections 40, 42, 44, 46.

Headboard Assembly with Environment Controls

Figure 2A:
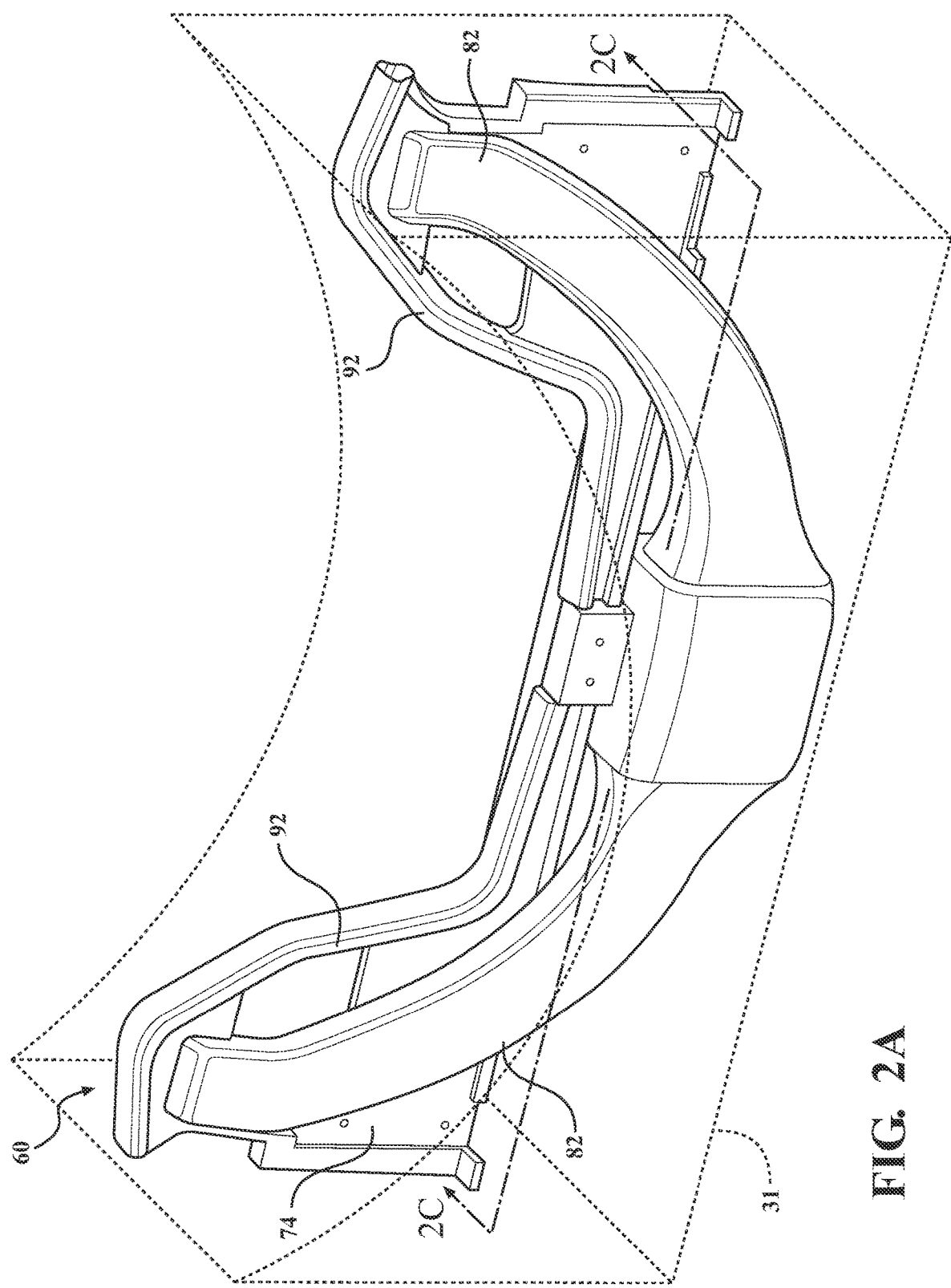
FIG. 2A is a rear perspective view of a headboard assembly of the patient support apparatus according to a first embodiment.

Referring now to FIG. 2A, a rear perspective view of the headboard assembly 60 of the patient support apparatus 30 according to a first embodiment is shown. The headboard assembly 60 is coupled to the support structure 32. In the embodiment shown, the headboard assembly 60 is coupled to the fowler section 40 and arranged adjacent to a head of the patient when the patient is lying on the patient support deck 38 (see FIG. 1A). The headboard assembly 60 may be connected to the fowler section 40 via fasteners, mating features (such as posts on the fowler section 40 and corresponding receivers on the headboard assembly 60), or the like. The headboard assembly 60 may be fixed to the fowler section 40 or easily removable. In other embodiments, the headboard assembly 60 may be coupled to the base 34, support frame 36, or other suitable location on the patient support apparatus 30.

In one embodiment, headboard assembly 60 may be contained within a headboard assembly cover 31, which may be of any suitable shape and size to cover the headboard assembly 60 in whole or in part. The headboard assembly cover 31 may be affixed to the headboard assembly 60 and/or any suitable component of the patient support apparatus 30, such as the fowler section 40.

In the illustrated embodiment, at least a portion of the headboard assembly 60 is configured to articulate with the fowler section 40 when the fowler section 40 articulates relative to the support frame 36 and/or relative to another section, such as the seat section 42, the leg section 44, and/or the foot section 46. The headboard assembly 60 comprises a headboard body 74 connected to the fowler section 40 to articulate with the fowler section 40. Owing to the connection between the headboard body 74 and the fowler section 40, the headboard assembly 60 maintains a relatively consistent positional relationship to the patient during various articulations of the patient support apparatus 30. For instance, when the fowler section 40 is being raised so that the patient is more upright, the headboard assembly 60 remains adjacent to the head of the patient so that the patient and/or caregiver can continue to utilize the below-described features of the headboard assembly 60.

Figure 2B:
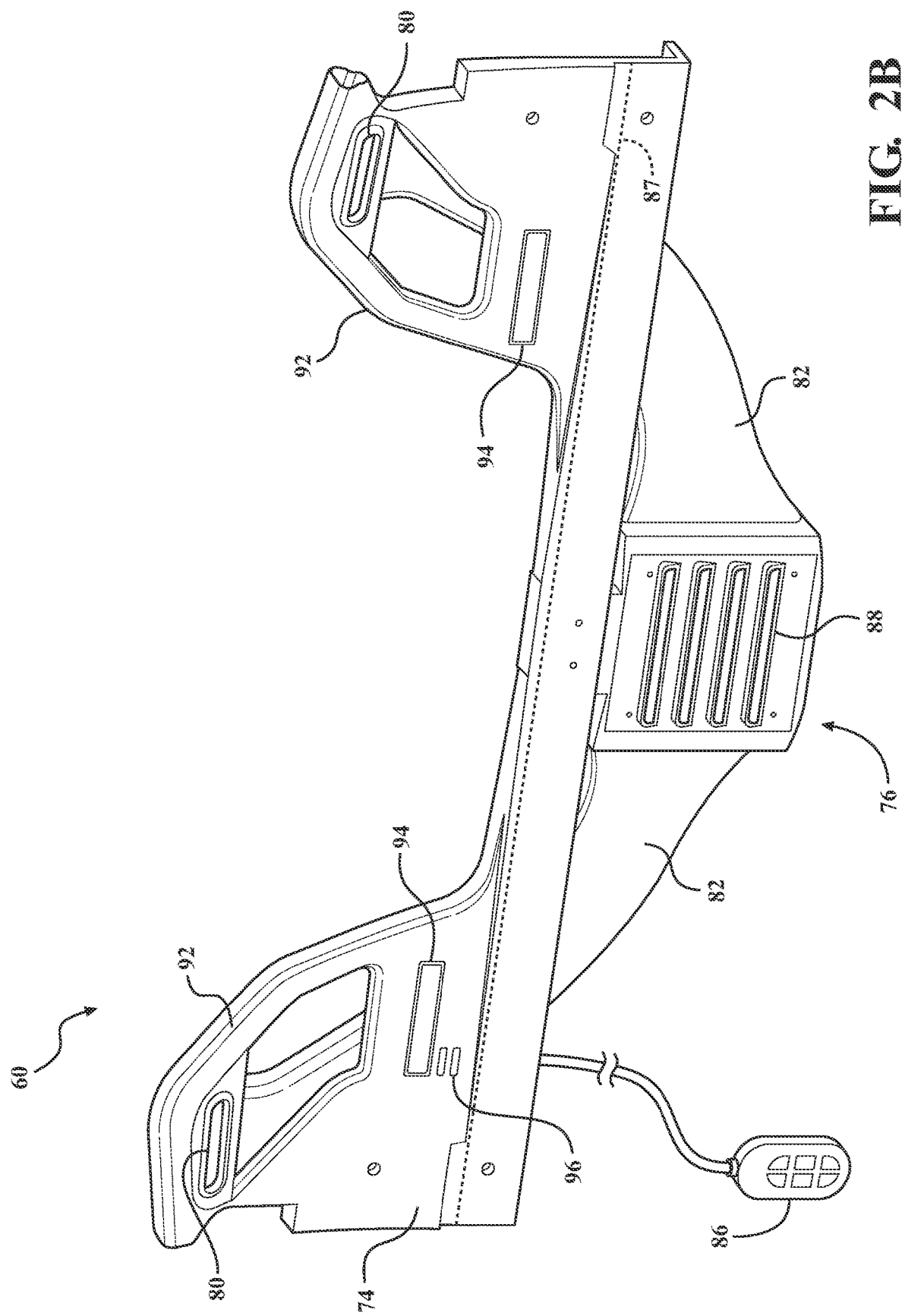
FIG. 2B is a front perspective view of a headboard assembly of the patient support apparatus according to the first embodiment.

Referring now to FIG. 2B, a front perspective view of the headboard assembly 60 according to the first embodiment is shown. The headboard assembly 60 comprises one or more environment controls 84 (not shown in FIG. 2B, see FIGS. 3A-3D). The one or more environment controls 84 are operable to alter an environment of the patient while the patient is present on the patient support deck 38. The one or more environment controls 84 may comprise a fan, a heater, a cooler, a speaker, a light source, a noise-cancelling feature, and/or other forms of environment controls. The headboard assembly 60 may further comprise a patient interface 86, such as a movable bed pendant (as shown in FIG. 2B). The patient interface 86 may be coupled to the one or more environment controls 84 to be controlled by the patient (see FIGS. 3A-D).

In one version, the headboard assembly 60 comprises a control module 76 to support the one or more environment controls 84. Additionally, or alternatively, environmental controls 84 may be supported or contained in other portions of the headboard assembly 60, separate from the control module 76. The control module 76 is coupled to the headboard body 74. The control module 76 is configured to be inserted into a central chamber 78 (see FIG. 2C) of the headboard body 74. The control module 76 may be modular such that control modules of different configurations are capable of coupling to the headboard body 74. The control module 76 may contain all circuitry and components of the environment controls 84 (such as fans/motors, speakers, heating/cooling elements, etc.), and combinations thereof. The control module 76 may be a self-contained unit for one or more of the environment controls 84 such that a particular control module 76 may be removed or added to the headboard assembly 60 and be fully operational without the need for additional equipment, components, or circuitry. Power may be routed to the headboard assembly 60 via the patient support apparatus 30. However, in certain embodiments, the control module 76 may have a separate power source, such as a battery. The control module 76 may be removably coupled to the headboard body 74 via fasteners, snap-fit connections, press-fit, or the like. The control module 76 may be sized and shaped for insertion into the central chamber 78 such that the control module 76 is relatively sealed about its periphery to the headboard body 74.

The headboard body 74 comprises one or more walls that define ports 80 and one or more ducts 82 that define main passageways 83 extending from the central chamber 78 to the ports 80. The ports 80 may be in any suitable position on the headboard body 74. The main passageways 83 are configured to direct one or more outputs from the one or more environment controls 84 to the ports 80. In the illustrated embodiment, the headboard body 74 defines two ports 80 and two main passageways 83, as shown in FIGS. 2A-2C, but more or fewer ports and main passageways are also contemplated.

In one embodiment, the mattress 50 may be flush with the hidden elevation line 87 shown in FIG. 2B such that it may cover the control module 76 entirely. The ports 80 are located so that they open above the top of the mattress 50. In one specific example, the ports 80 may be located approximately 6 inches above the top of the mattress 50 so that the ports 80 are above but near the patient's head when the patient is laying on the mattress 50. In embodiments that include the headboard assembly cover 31, the headboard assembly cover 31 will include apertures to accommodate the ports 80. In some versions, it may be desirable for the ports 80 to be located below a top surface of the mattress 50.

Referring now to FIG. 2C, a cross-sectional view of the headboard assembly 60 according to FIG. 2A is shown, where the one or more environment controls 84 comprises a speaker 103. The speaker 103 (see also FIG. 3D) may be contained within the central chamber 78. In the version shown, the central chamber 78 comprises an internal sound deflector 90, which may also be referred to as a horn. The speaker 103 produces sound, which is carried through the internal sound deflector 90 into the main passageways 83 via hollow deflector passageways 91. The deflector passageways 91 extend from the speaker 103 to outlets 91a. The sound is delivered from the speaker 103, through the deflector passageways 91, through the main passageways 83, to the patient via ports 80. Walls, such as plastic walls, separate the deflector passageways 91 from the main passageways 83, except at the outlets 91a. The use of the internal sound deflector 90 allows diversion of the sound while still providing the main passageways 83 for airflow when a fan unit and/or heater/cooler is used simultaneously. The speaker system is discussed in more detail below with regard to FIG. 3D.

Figure 3A:
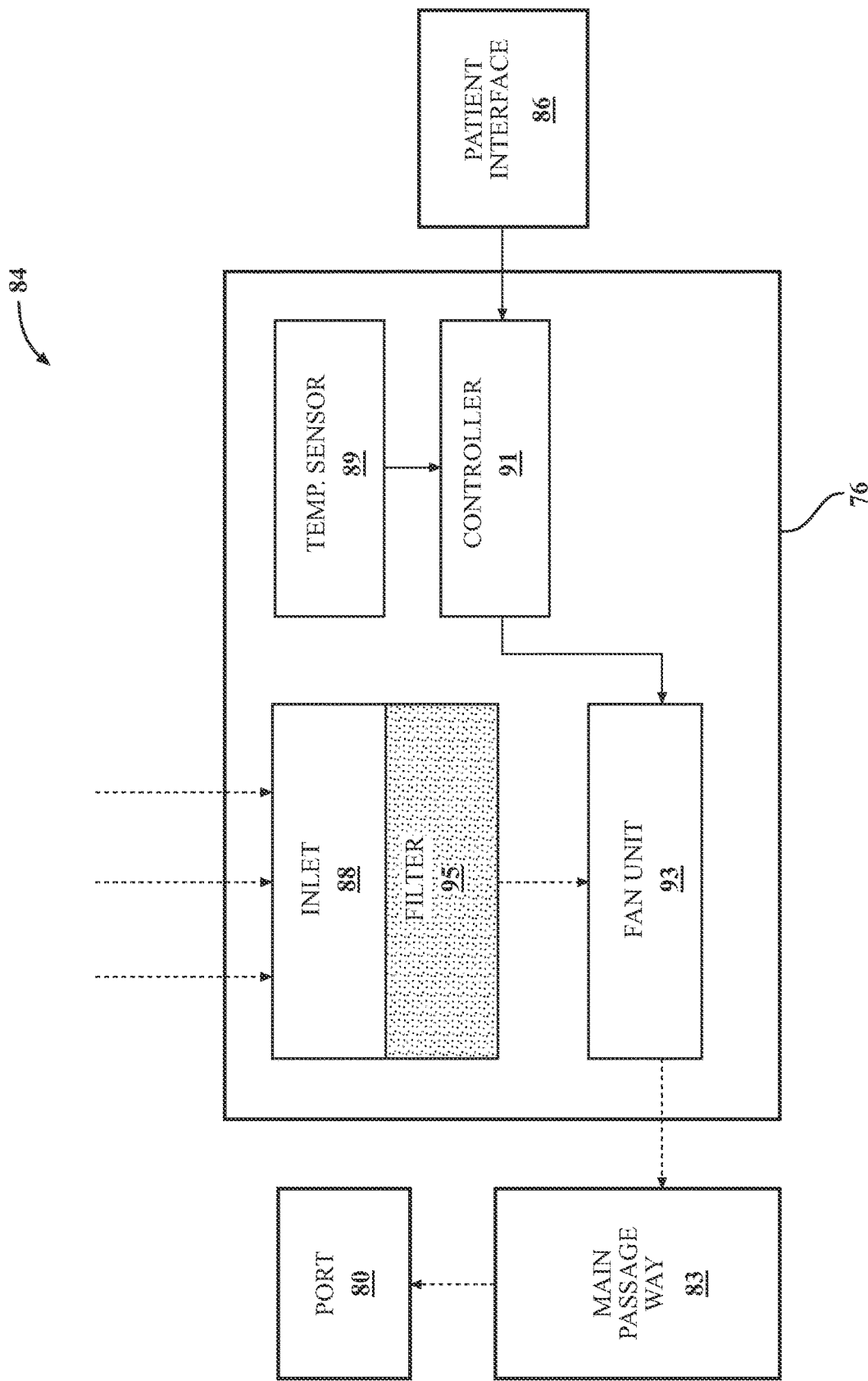
FIG. 3A is a diagram illustrating an environment control of the headboard assembly according to the first embodiment comprising a fan.

Referring now to FIG. 3A, a diagram illustrating an environment control 84 comprising a fan unit 93 is shown. Airflow connections (dashed) and electrical connections (solid) are illustrated in FIG. 3A. The control module 76 may comprise an inlet 88 to receive air from the outside environment (dashed lines with arrows are used to illustrate direction of air flow). The control module 76 may further comprise a temperature sensor 89 for monitoring the temperature of the air. If the temperature sensor 89 senses a temperature above a certain threshold, a controller 91 connected to the temperature sensor 89 may operate the fan unit 93 in order to lower the ambient temperature for the patient. In certain embodiments, the patient may use the patient interface 86 to send a signal to the controller 91 to initiate the fan unit 93. Once the controller 91 has received a signal to initiate the fan unit 93, the controller 91 activates the fan unit 93. The fan unit 93 may comprise a motor and blades that pull additional air through the inlet 88, and through a filter 95, which may be, for example, a HEPA filter, disposed between the inlet 88 and the main passageways 83. The air passes through the filter 95 and into the main passageways 83, for eventual passage through the ports 80. The filter 95 may be absent in certain embodiments. In certain embodiments, the patient may control a speed of the fan unit 93 using the patient interface 86.

Figure 3B:
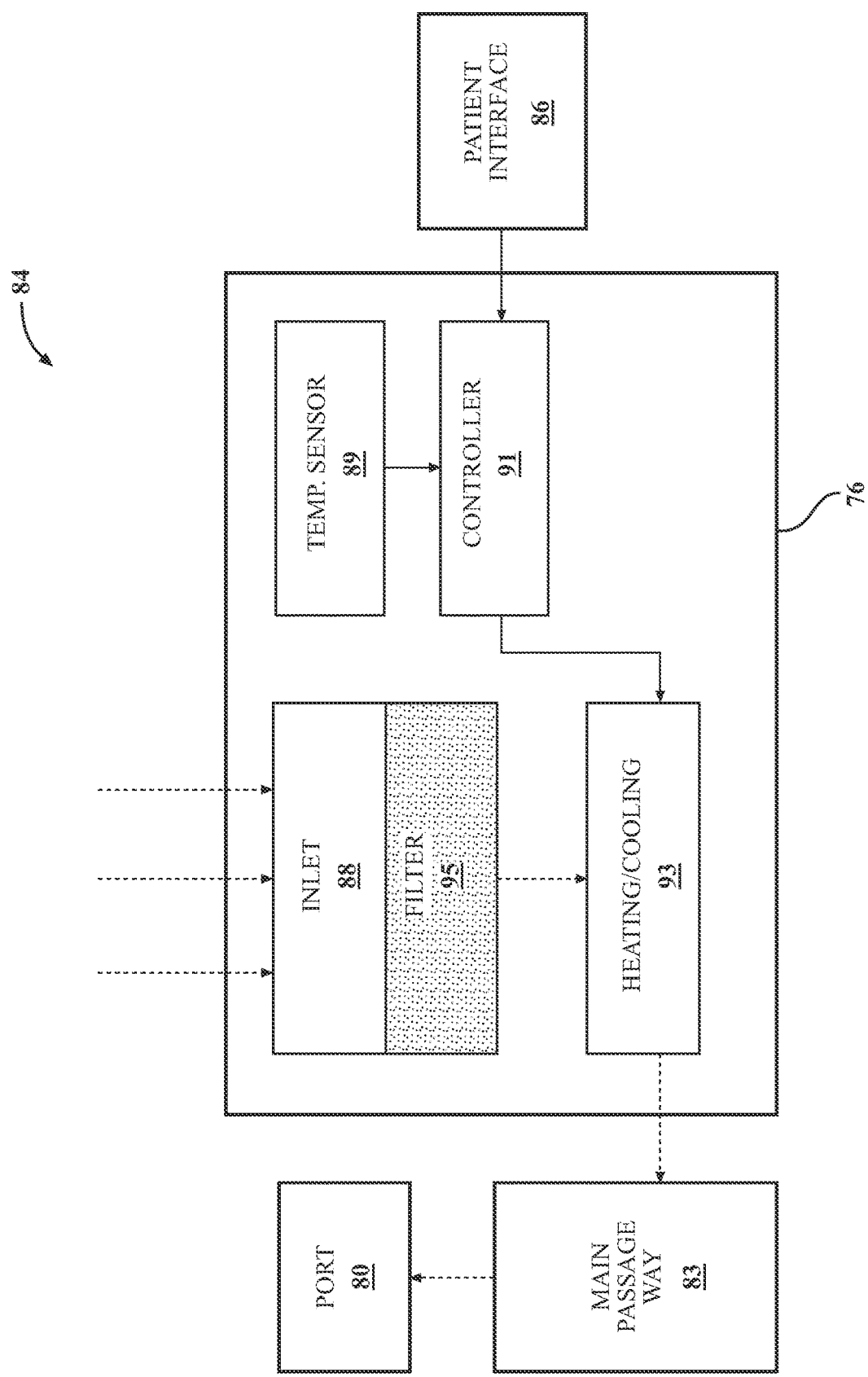
FIG. 3B is a diagram illustrating an environment control of the headboard assembly according to the first embodiment comprising a heating/cooling system.

Referring now to FIG. 3B, a diagram illustrating an environment control 84 comprising a heating/cooling system is shown. Airflow connections (dashed) and electrical connections (solid) are illustrated in FIG. 3B. The control module 76 may comprise the inlet 88 to receive air from the outside environment (dashed lines with arrows are used to illustrate direction of air flow). The control module 76 may further comprise the temperature sensor 89 for monitoring the temperature of the air. If the temperature sensor 89 senses a temperature above or below a certain threshold, the controller 91 connected to the temperature sensor 89 may operate the heating/cooling system in order to lower or raise the ambient temperature for the patient. In certain embodiments, the patient may use the patient interface 86 to send a signal to the controller 91 to operate the heating/cooling system. Once the controller 91 has received a signal to operate the heating/cooling system, the controller 91 activates a heating/cooling element 97. In some embodiments, the heating/cooling element 97 may comprise a resistive heating element, a thermoelectric device (such as a Peltier device), or other suitable heating and/or cooling elements. The heating/cooling element 97 heats or cools the air received from the inlet 88. The heating/cooling element 97 is disposed between the inlet 88 and the main passageways 83. The heated/cooled air passes through the main passageways 83 for eventual passage through the ports 80. Filter 95 may filter the air before or after the air is heated/cooled and may be absent in some embodiments. In certain embodiments, the patient may use the patient interface 86 to increase/decrease the ambient temperature. In some embodiments, there may be preset limits on the temperature to avoid excessively high or low temperatures that might endanger the patient.

Figure 3C:
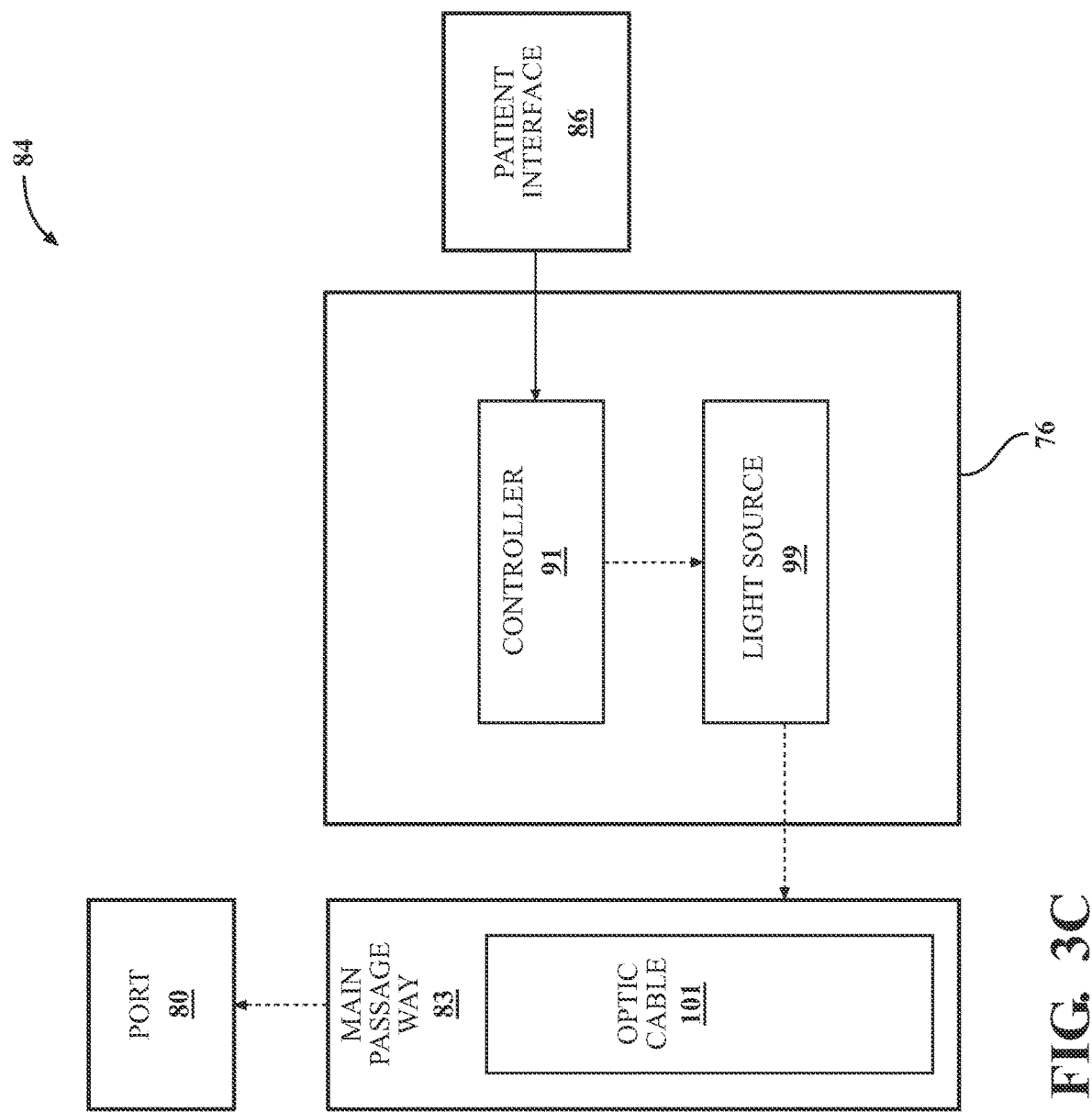
FIG. 3C is a diagram illustrating an environment control of the headboard assembly according to the first embodiment comprising a lighting system.

Referring now to FIG. 3C, a diagram illustrating an environment control 84 comprising a lighting system is shown. The control module 76 comprises the controller 91 and a light source 99. The patient may use the patient interface 86 to send a signal to the controller 91 to operate the lighting system. The controller 91 activates the light source 99, which produces light. The light source 99 sends the light to one or more optic cables 101 (dashed lines with arrows are used to illustrate direction of the light) within the main passageways 83, for eventual passage through the ports 80. Using optic cables 101 eliminates the need for electrical circuitry through the main passageways 83 up to the ports 80. It also allows for upgrading the light source 99 easily and inexpensively. Other light sources and structure for routing light from the light source to the patient are also contemplated.

Figure 3D:
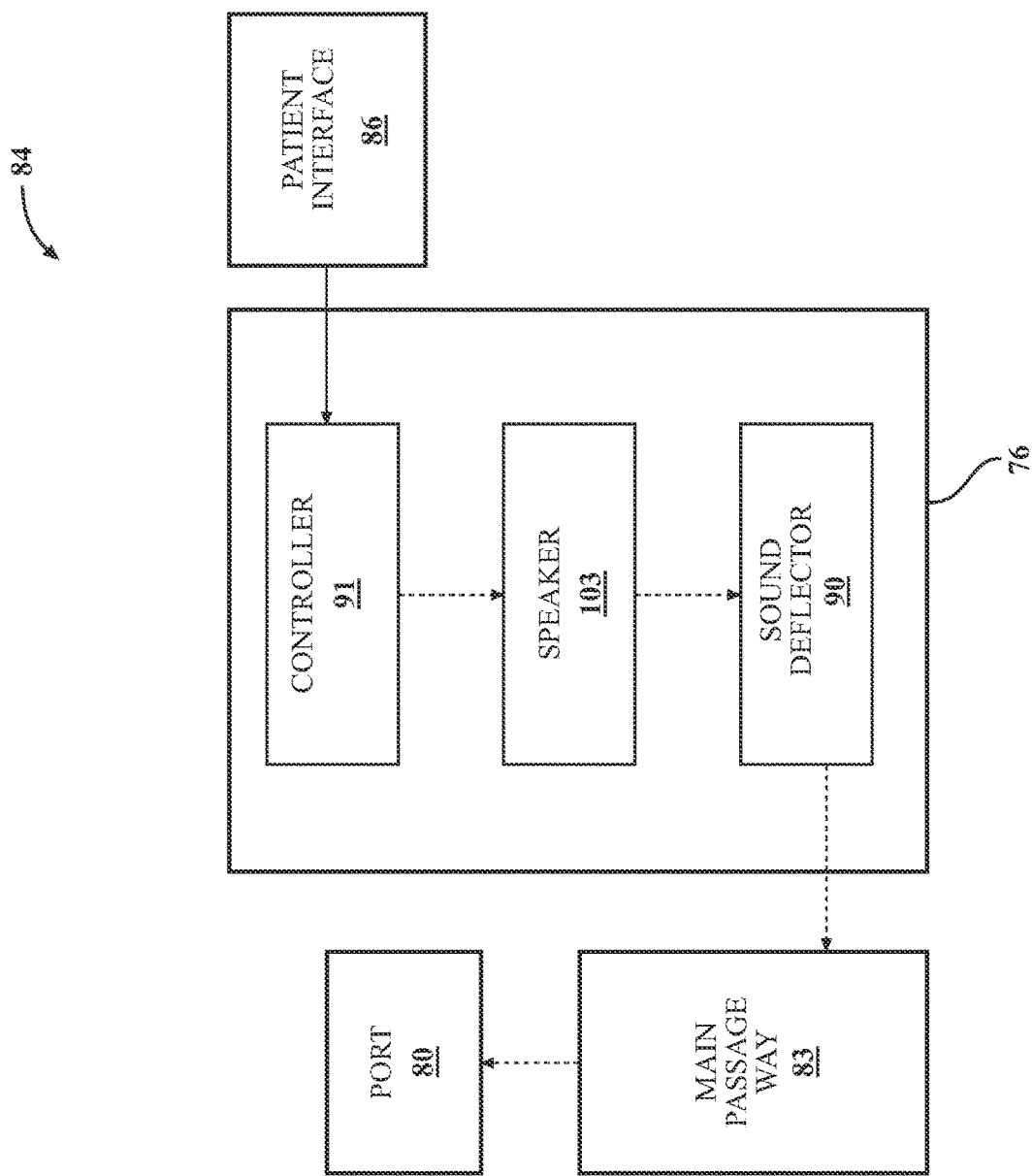
FIG. 3D is a diagram illustrating an environment control of the headboard assembly according to the first embodiment comprising a speaker system.

Referring now to FIG. 3D, a diagram illustrating an environment control 84 comprising a speaker system is shown. The control module 76 comprises the controller 91 and the speaker 103 discussed above. The patient may use the patient interface 86 to send a signal to the controller 91 to operate the speaker system. The controller 91 activates the speaker 103, which produces sound. The speaker 103 sends the sound (dashed lines with arrows are used to illustrate direction of the sound) through the internal sound deflector 90 into the main passageways 83 via the hollow deflector passageways 91. The sound is delivered to the patient via the ports 80. In certain embodiments, the patient may control a volume of the speaker 103 using the patient interface 86. In some embodiments, the volume of the speaker 103 may have preset limits to avoid excessively high volumes that might disturb other patients or interfere with caregivers' ability to hear important information (e.g., intercom announcements, vital sounds, code alerts, etc.).

It will be understood that any combination of environment controls 84 may be integrated into a single headboard 60 within a single module, or integrated into a single headboard 60 or multiple headboards 60 within multiple, separate modules. It should also be appreciated that although airflow, light, and sound are illustrated as all being routed from the control module 76 to the same ports 80, separate ports 80 and/or separate main passageways 82 may be provided to separately route airflow, light, and/or sound to the patient. Various combinations of ports, passageways, and environment controls are contemplated.

Referring again to FIG. 2B, the headboard assembly 60 may further comprise one or more retainers 94 coupled to the headboard body 74. The retainers 94 may be configured to retain pillows and/or mattress 50. The retainers 94 may be made of a rubber-like membrane or other non-slip material. The retainers 94 are described in more detail below with reference to FIG. 5B.

The headboard assembly 60 may further comprise one or more patient handles 92 that are arranged to be grasped by the patient when lying on the patient support deck 38. The patient handles 92 may be arranged on the headboard body 74 (as shown) or any other suitable location. The patient handles 92 may optionally be used for holding physical therapy bands or restraints, or for management of patient lines such as oxygen and IV lines. The patient handles 92 may be used by the patient for self-readjustment on the patient support deck 38 after the patient has slipped or is in an otherwise uncomfortable position. The headboard assembly 60 may further comprise one or more charging ports 96, such as USB ports, or other data/power ports. The charging ports 96 may be located in any suitable position on the headboard assembly 60 that is easily accessible to the patient, such as, for instance, on the headboard body 74. The charging ports 96 may be used for charging portable electronic devices.

Headboard Assembly with Articulating Arm

Figure 4A:
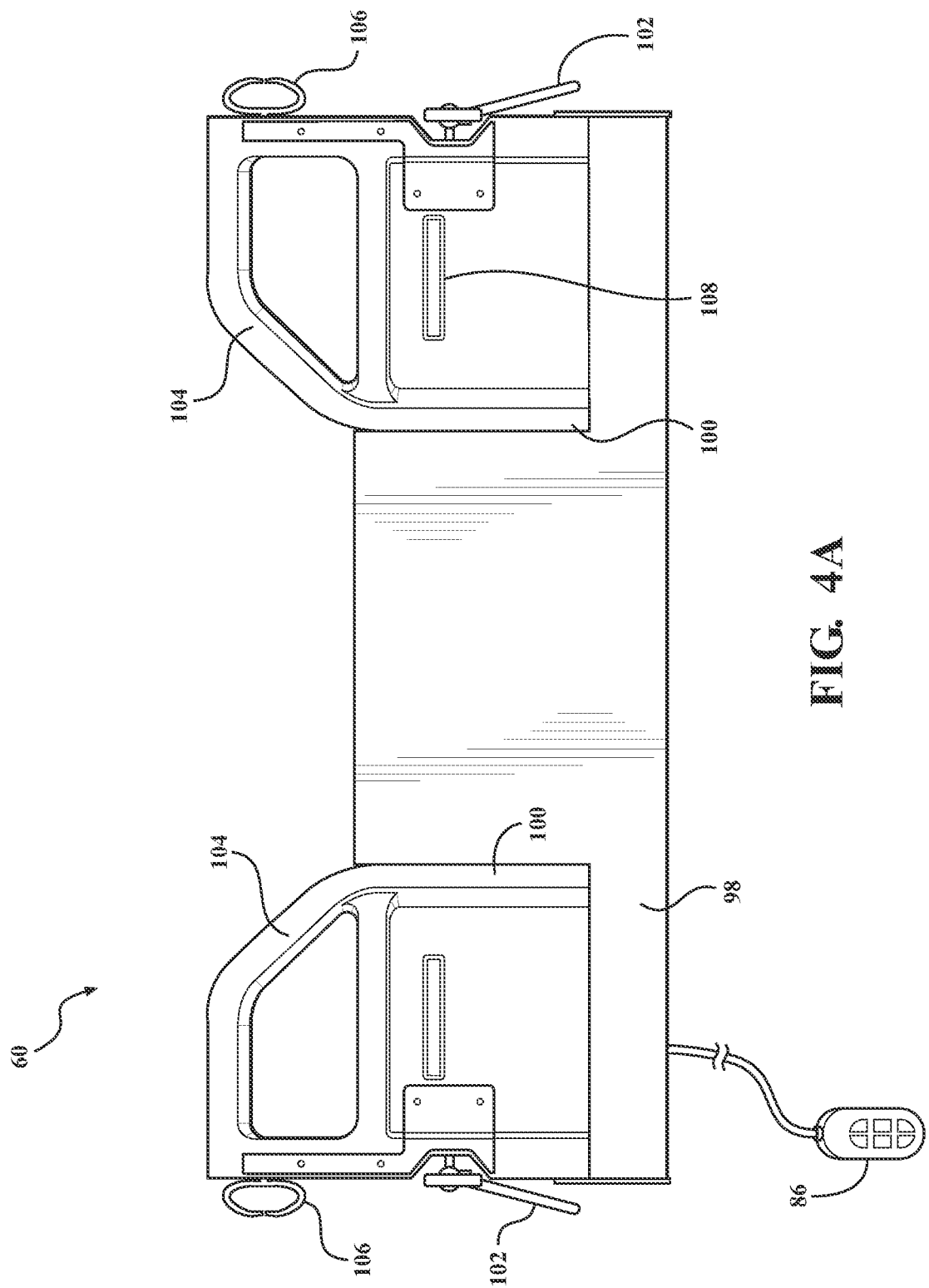
FIG. 4A is a front view of a modular headboard assembly of the patient support apparatus according to a second embodiment.

Referring now to FIG. 4A, the headboard assembly 60 according to a second embodiment is shown. The headboard assembly 60 may be coupled to the support structure 32 in the same manner as previously described for the first embodiment. In the second embodiment, the headboard assembly 60 is coupled to the fowler section 40 and arranged adjacent to a head of the patient when the patient is lying on the patient support deck 38 (see FIG. 1A) such that the headboard assembly 60 moves in conjunction with the fowler section 40. In other embodiments, the headboard assembly 60 may be coupled to the base 34, support frame 36, or other suitable location on the patient support apparatus 30.

The headboard assembly 60 may comprise a headboard body 98 and one or more modular headboard sections 100. Each of the modular headboard sections 100 is coupled to an articulating arm 102 (see also FIGS. 4B-C). The articulating arm 102 may be configured to articulate independently of the articulation between the fowler section 40 and the support frame 36 and/or between the fowler section 40 and another section, such as the seat section 42, the leg section 44, and/or the foot section 46. The articulating arm 102 is configured to articulate to allow movement of the modular headboard section 100 into a variety of configurations. Although two modular headboard sections 100 are illustrated, only one will be described in detail.

Figure 4B:
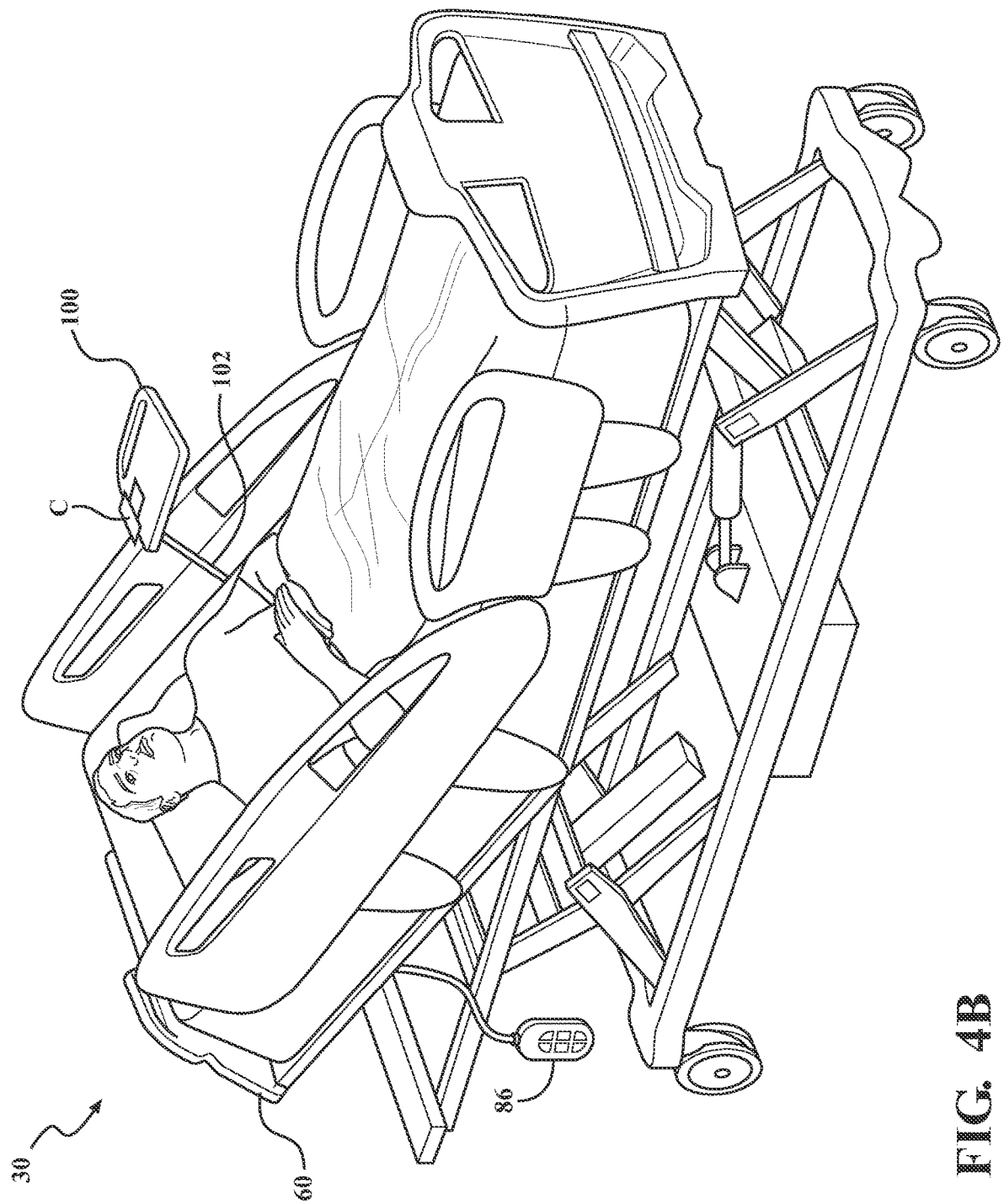
FIG. 4B illustrates a first configuration of a modular headboard assembly according to the second embodiment.

Referring now to FIG. 4B, a first configuration of the modular headboard 100 is shown. The articulating arm 102 may be configured to articulate to allow movement of the modular headboard section 100 into the first configuration. In the first configuration, the modular headboard section 100 is articulated away from the fowler section 40 and toward the foot end of patient support apparatus 30. The modular headboard section 100 is further pivoted approximately 90 degrees to provide a functional work surface for a caregiver. In the first configuration, the caregiver can use the modular headboard section 100 as a temporary tray or table for writing or for placing various items while working with the patient. In some versions, the modular headboard section 100 comprises a clip C integrated into the modular headboard section 100. The clip C, or other form of bracket or securing mechanism, is provided for holding items, such as paperwork, books, magazines, portable electronic devices, and the like. The clip C may be like that used on clipboards and comprises a clamp pivotally mounted to a surface of the modular headboard section 100 and biased into a clamped state by a spring (not shown).

Figure 4C:
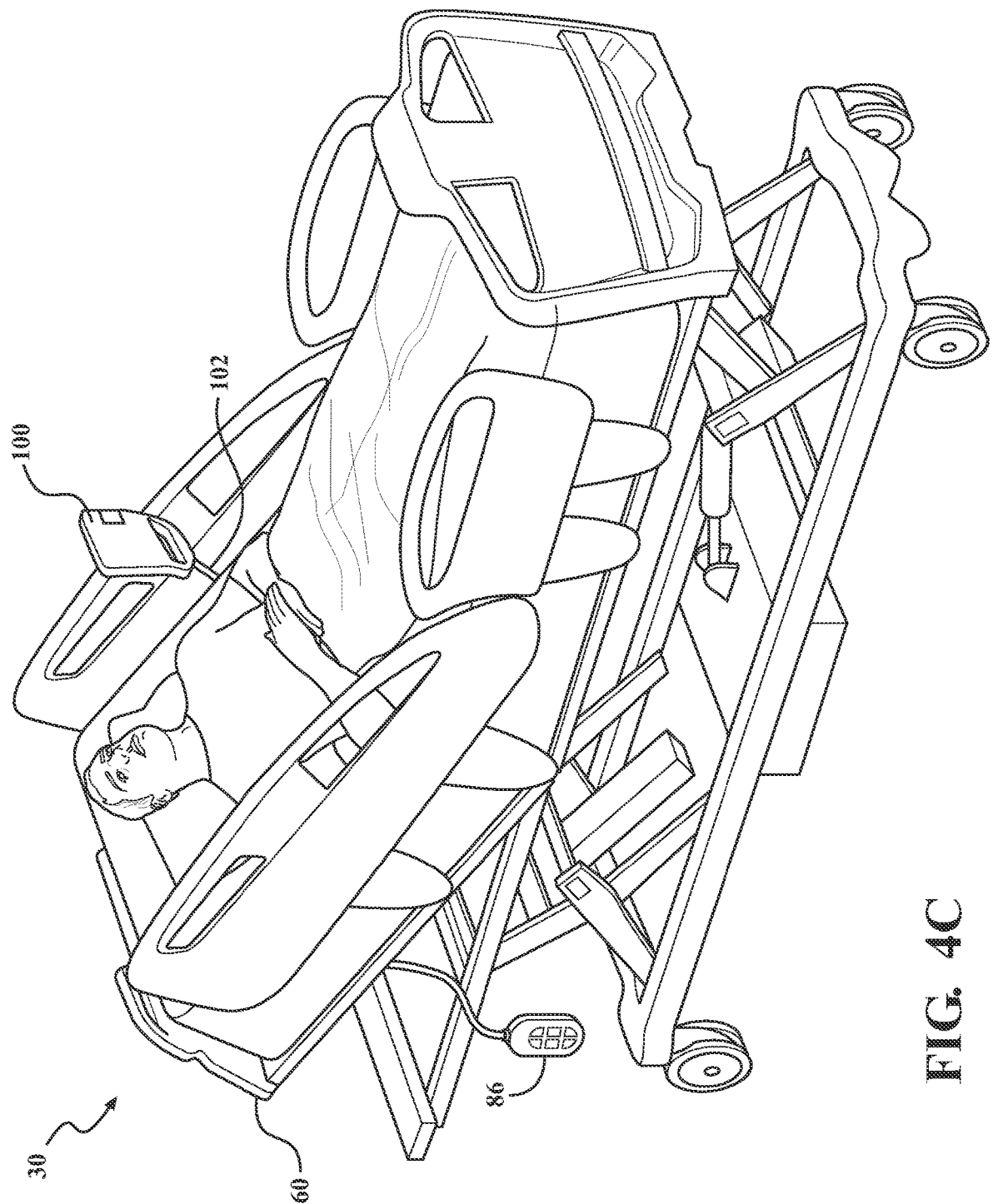
FIG. 4C illustrates a second configuration of the modular headboard assembly according to the second embodiment.

Referring now to FIG. 4C, a second configuration of the modular headboard section 100 is shown. The articulating arm 102 may be configured to articulate to allow movement of the modular headboard section 100 into the second configuration. In the second configuration, the modular headboard section 100 is articulated away from the fowler section 40 and toward the foot end of patient apparatus 30. The modular headboard section 100 is further pivoted approximately 180 degrees to provide a functional work surface for the patient positioned on the patient support deck 38. In the second configuration, the patient can use the modular headboard section 100 (including the clip C) as a work surface for holding a portable electronic device such as a cell phone or a tablet, books or other reading material, a bed pendant, or patient lines (e.g., IV lines).

Figure 4D:
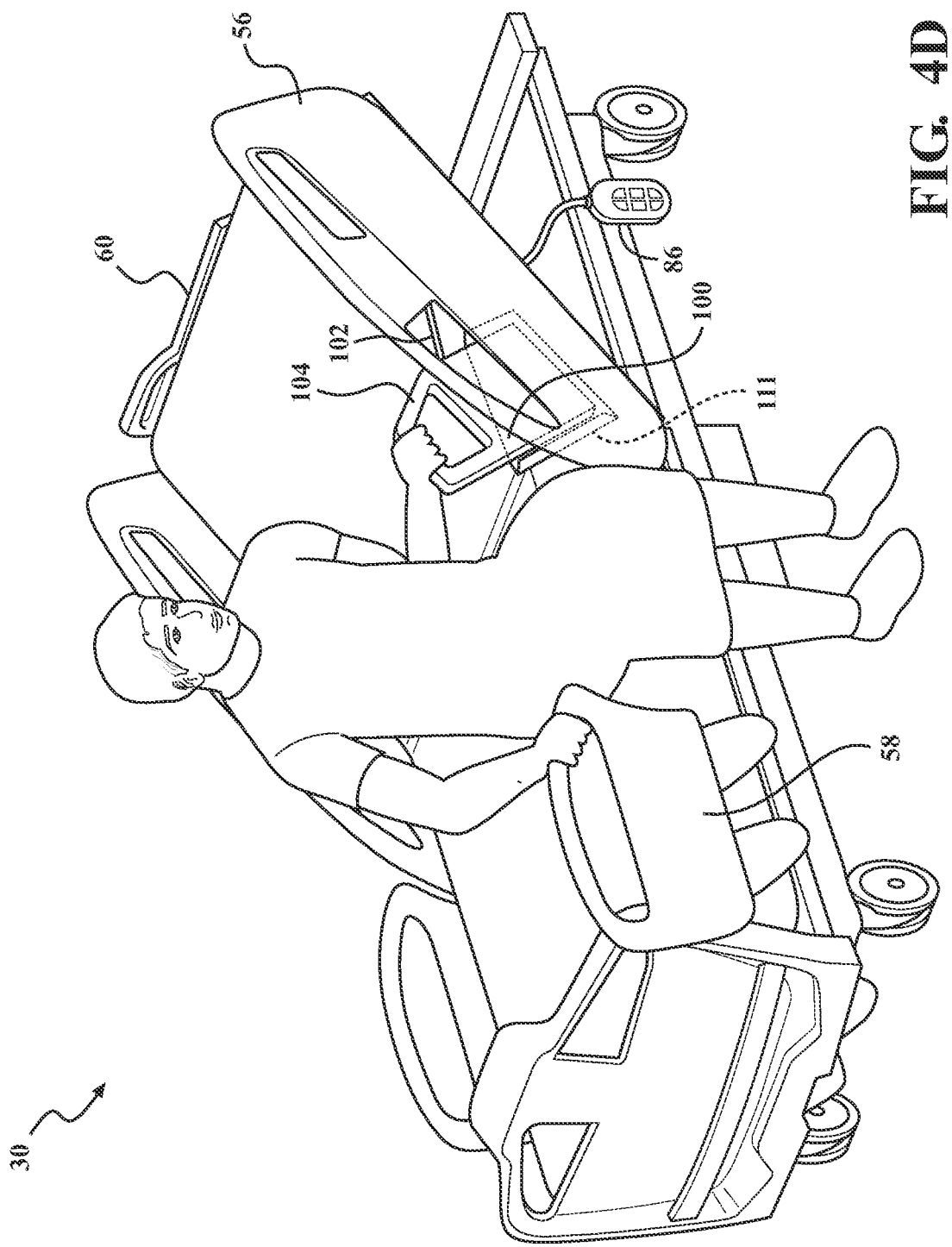
FIG. 4D illustrates a third configuration of the modular headboard assembly according to the second embodiment.

Referring now to FIG. 4D, a third configuration of the modular headboard 100 is shown. The articulating arm 102 may be configured to articulate to allow movement of the modular headboard section 100 into the third configuration. In the third configuration, the modular headboard section 100 is articulated away from the fowler section 40 and toward the side of patient support apparatus 30. The modular headboard section 100 is further pivoted to be adjacent to side rail 56. In the third configuration, the patient can use the modular headboard section 100, and the patient handle 104 thereof, as an additional ingress/egress aid to assist the patient entering or exiting patient support apparatus 30. The position of the modular headboard section 100 provides a more ergonomic hand placement. The third configuration may also be used when the patient is already lying on the patient support deck 38, to assist the patient with self-readjustment on the patient support deck 38 after the patient has slipped or is in an otherwise uncomfortable position.

Figure 4E:
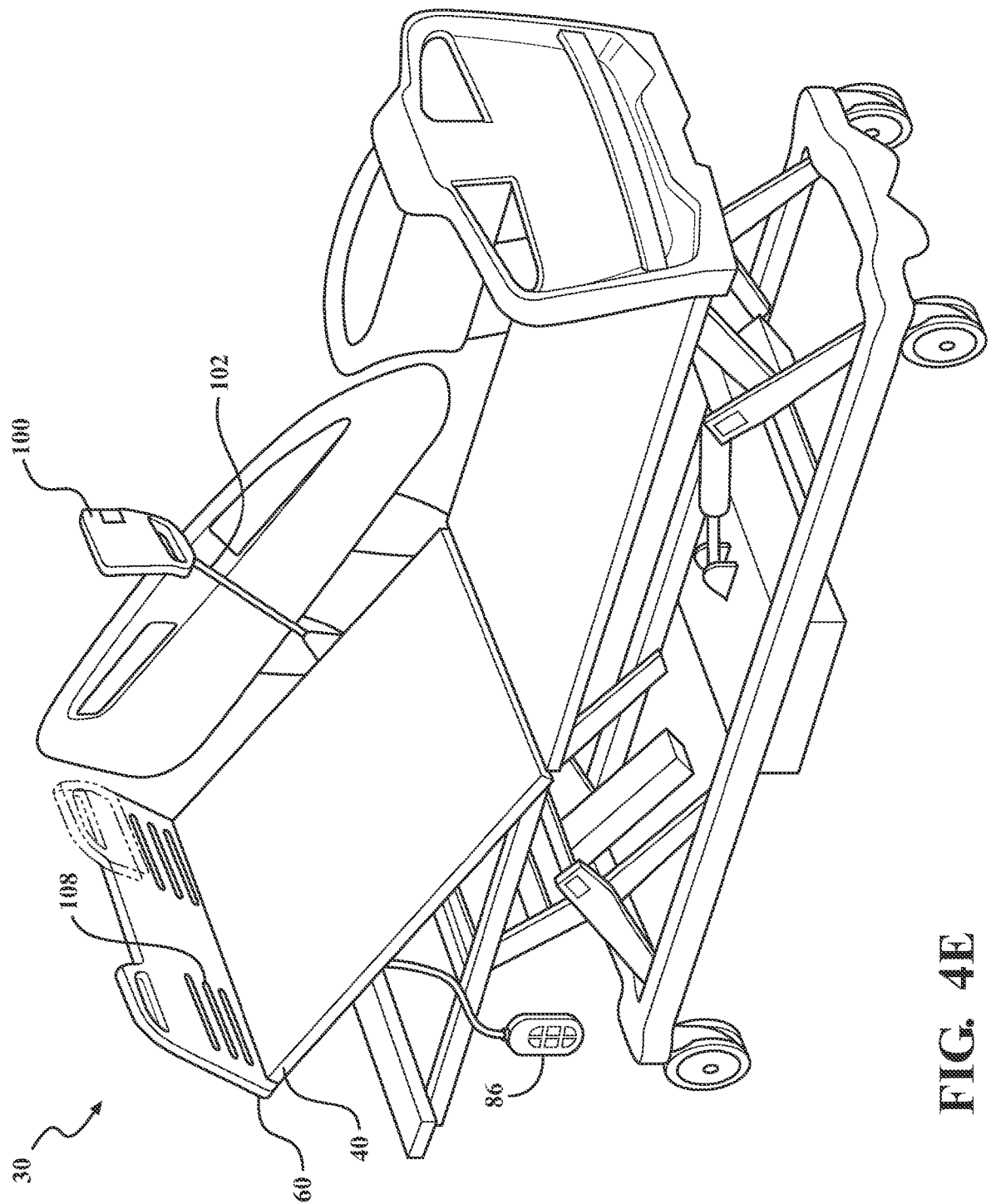
FIG. 4E illustrates a perspective view of the patient support apparatus including the modular headboard assembly according to the second embodiment.
Figure 4F:
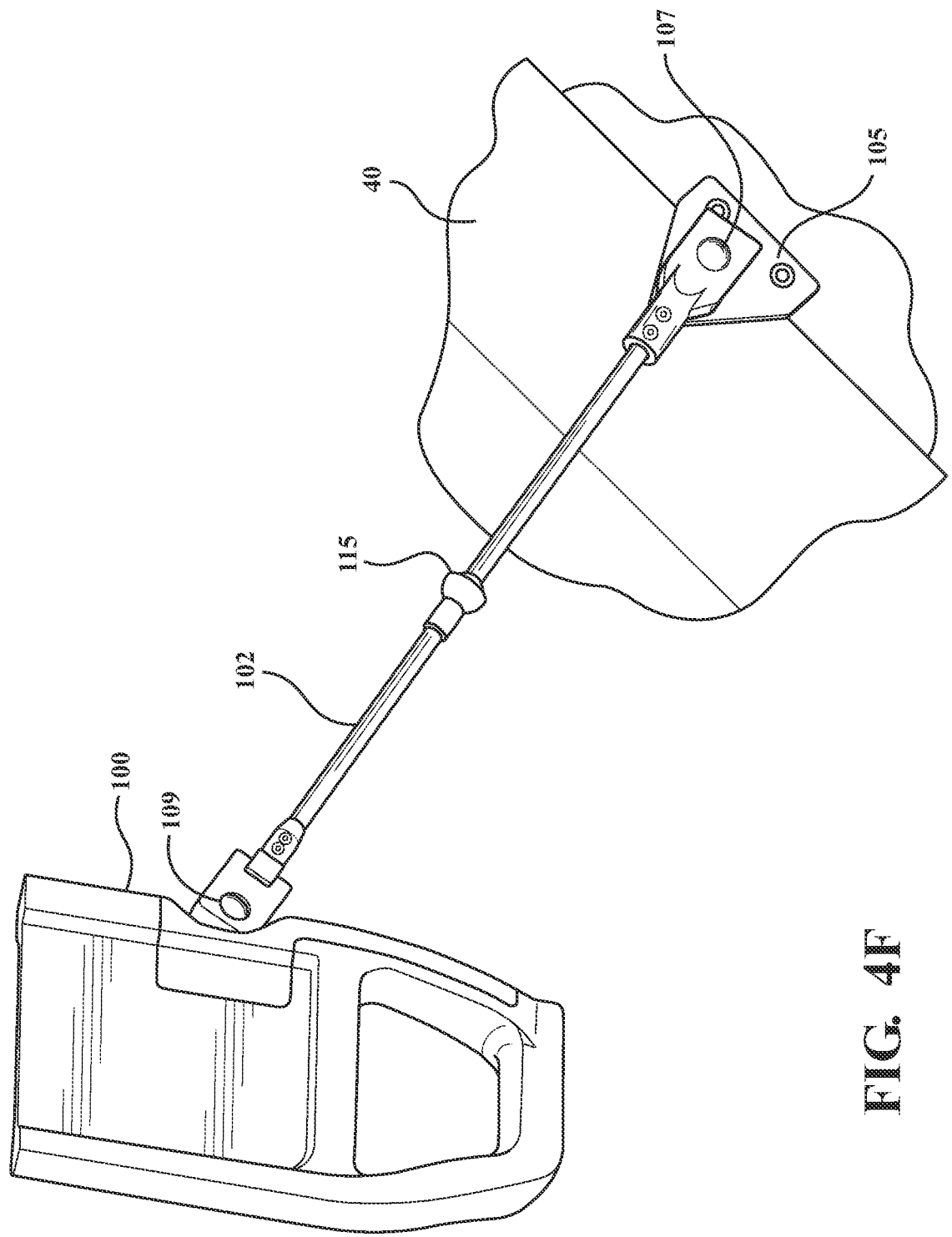
FIG. 4F illustrates a perspective view of an articulating arm of the modular headboard according to the second embodiment.

Referring now to FIGS. 4E-4F, views of the articulating arm 102 attached to the modular headboard section 100 according the second embodiment are shown. FIG. 4E illustrates a perspective view of the patient support apparatus 30, including the modular headboard assembly according to the second embodiment is shown. FIG. 4F shows a perspective view of the articulating arm 102 attached to the modular headboard section 100.

In the embodiment shown, the articulating arm 102 is mounted to the fowler section 40 via mounting bracket 105 at a first joint 107, which may be a ball and socket joint or other type of joint, that allows the articulating arm 102 to pivot about the mounting bracket 105. In other embodiments, the articulating arm 102 may be mounted directly to the support frame 36 or any other suitable location on the patient support apparatus 30.

The articulating arm 102 is mounted to the modular headboard section 100 at a second joint 109, which may be a ball and socket joint or other type of joint, which allows the modular headboard section 100 to pivot about the articulating arm 102 into the various configurations described herein. Additional and/or alternative joints, such as joint 115, may be provided along the articulating arm 102 to provide additional freedom of movement of the modular headboard section 100 to place the modular headboard section 100 into the various configuration shown or other configurations.

Locks (not shown) may be associated with the joints to lock the joints from movement once the modular headboard section 100 is placed in a desired configuration. Additionally or alternatively, the joints may be formed with sufficient friction to hold the modular headboard section 100 in any configuration in which it is positioned so that the modular headboard section 100 remains at the desired configuration until actively moved. Furthermore, the headboard body 98, fowler section 40, or other locations may comprise a receiver 111 (see FIG. 4D) sized and shaped to receive the modular headboard section 100 in certain configurations so that the modular headboard section 100 is constrained from movement in one or more degrees of freedom. For instance, the receiver 111 may comprise a pocket sized for slidably receiving a bottom portion of the modular headboard section 100 to limit lateral movement of the modular headboard section 100 when used for ingress/egress. Although use of the receiver 111 is shown in the illustrated embodiment of FIG. 4D, it will be understood that any suitable means of supporting the articulating arm 102 may be used instead of or in addition to the receiver 111. After the modular headboard 100 has been moved into the first, second, or third configurations, the patient or the nurse can use the articulating arm 102 to rotate the modular headboard 100 back into a stowed position on the headboard assembly 60.

In one embodiment, modular headboard 100 may not be attached to the articulating arm 102. Instead, the modular headboard 100 may be entirely independent from the patient support apparatus 30 and may simply be stowed on the headboard assembly 60 and removed and used as needed by the patient or caregiver.

The headboard assembly 60 may further comprise one or more patient handles 104 that are arranged to be grasped by the patient when the patient is lying on the patient support deck 38. The patient handles 104 may be arranged on the modular headboard section 100 (as shown) or any other suitable location. The patient handles 104 may optionally be used for holding physical therapy bands or restraints, or for management of patient lines such as oxygen and IV lines. Alternatively or in addition, the headboard assembly 60 may further comprise a separate line management loop 106, which may be used to retain and manage patient lines such as oxygen and IV lines. The patient handles 104 may be used by the patient for self-readjustment on the patient support deck 38 after the patient has slipped or is in an otherwise uncomfortable position.

The headboard assembly 60 may further comprise one or more retainers 108. The retainers 108 may be arranged on the modular headboard sections 100 (as shown), the headboard body 98, or any suitable location. The retainers 108 may be configured to retain pillows and/or mattress 50. The retainers 108 may be made of a rubber-like membrane or other non-slip material. The retainers 108 are described in more detail below with reference to FIG. 5B.

Alternative Headboard Assembly

Figure 5C:
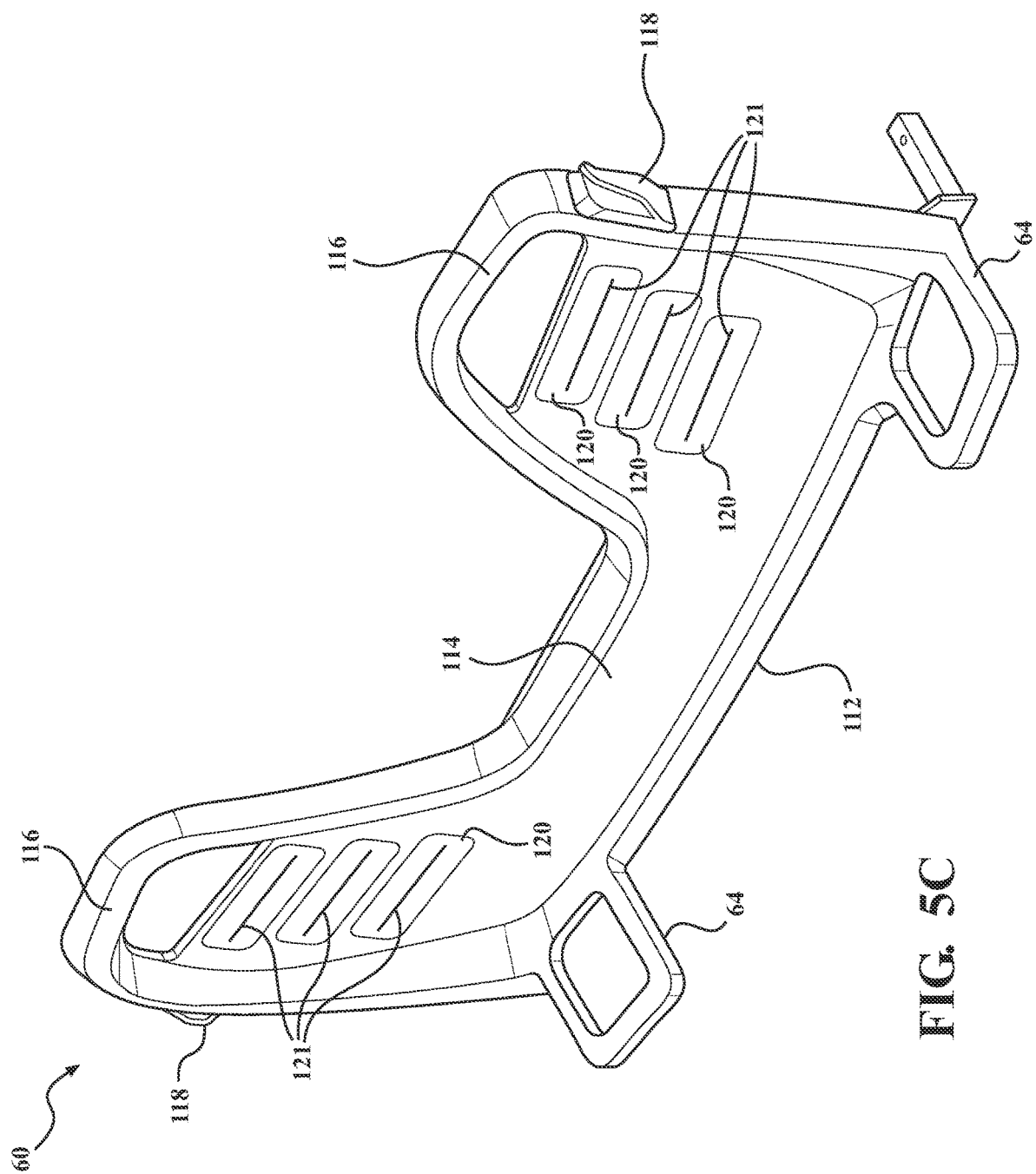
FIG. 5C is a rear perspective view of the headboard assembly according to the third embodiment.

Referring now to FIGS. 5A-5C, front perspective and rear perspective views of the headboard assembly 60 according to a third embodiment are shown. The headboard assembly 60 is coupled to the support structure 32 in the same manner as previously described above for the other embodiments. In the embodiment shown, the headboard assembly 60 is coupled to the fowler section 40 and arranged adjacent to a head of the patient when the patient is lying on the patient support deck 38 (see FIG. 1A) such that the headboard assembly 60 moves in conjunction with the fowler section 40. The headboard assembly 60 comprises a headboard body 110 having a base portion 112 coupled to the fowler section 40. The headboard assembly 60 further comprises a barrier portion 114 extending from the base portion 112. In other embodiments, the headboard assembly 60 may be coupled to the base 34, support frame 36, or other suitable location on the patient support apparatus 30.

The headboard assembly 60 may further comprise one or more patient handles 116 that are arranged to be grasped by the patient when the patient is lying on the patient support deck 38. The patient handles 116 may be arranged on the barrier portion 114 (as shown) or any other suitable location. The patient handles 116 may optionally be used for holding physical therapy bands or restraints, or for management of patient lines such as oxygen and IV lines. The patient handles 116 may be used by the patient for self-readjustment on the patient support deck 38 after the patient has slipped or is in an otherwise uncomfortable position.

Alternatively or in addition, the headboard assembly 60 may further comprise a separate line management loop or hook 118, which may be used to retain and manage patient lines such as oxygen and IV lines. The caregiver interface 64 may be located at the base portion 112.

Referring now to FIG. 5B, a front perspective view of the headboard assembly according to the third embodiment illustrating operation of retainers 120 is shown. It will be understood that this description also applies to operation of retainers 94 and 108. In the embodiment shown, pillowcase fabric 113 is pushed into a front side of retainers 120 and pulled out through a back side of retainers 120. It will be understood that any fabric, such as sheets, mattress cover fabric, or even the pillow or mattress itself, may be retained by retainers 120 in place of pillowcase fabric 113. The retainers 120 may be made of a rubber-like membrane or other non-slip material such that once the fabric 113 is pulled through the retainers 120, the fabric 113 will remain in place and must be removed by pulling forcibly by hand. This reduces patient discomfort caused by slipping and clumping of pillows, sheets, and other linens, which the patient may be physically unable to readjust without assistance from the caregiver or without causing significant pain and, in some cases, endangering the patient. Each of the retainers 120 shown in FIGS. 5A and 5B comprise a resilient membrane having a slit 121 for receiving the material to be retained. The membrane is flexible to receive the material through the slit 121 (by pushing the material through the slit 121 on one side and/or pulling the material into the slit 121 on the other side). The membrane is configured so that the slit 121 is normally closed in the absence of any material so that once the material is received in the slit 121, the slit 121 is biased against the material to retain the material in place.

In some embodiments, the headboard assembly 60 may include parallel retainers 120 in a stacked configuration to accommodate differing heights of materials (pillows, mattresses, or other bedding). In FIG. 5C, the retainers 120 are shown in a stacked configuration, with a column of three retainers 120 on each side of headboard assembly 60. By way of example, when material to be retained by the retainer 120 has a greater height, the top retainers 120 may be used, whereas when the material height is low, the bottom retainers 120 may be used. Different retainers 120 in a column may be used to retain different layers at different heights (e.g., one holds a pillow, one holds a mattress below the pillow, etc.). It will be understood that any number of retainers 120 may be included in this stacked configuration.

Referring now to FIG. 5D, a partial side view of the headboard assembly 60 and mattress 50 according to the third embodiment is shown. Retainers 120 align with the mattress 50 at different heights (where the arrow indicates increasing height of the mattress 50). Depending on the height of the mattress 50, one or more retainers 120 may be used. It will be understood that, as illustrated, mattress 50 is interchangeable with any material to be retained by retainers 120 (bedding, pillows, etc.).

As shown in FIG. 5C, additional caregiver interfaces 64 may be connected to or integrated into the headboard body 110 to provide caregivers with additional locations to grasp and facilitate movement of the patient support apparatus 30. The caregiver interfaces 64, which are shown as handles in FIG. 5C, can be especially useful when the fowler section 40 is raised and the patient handles 116 are inaccessible to the caregiver, which may otherwise be used to manipulate and move the patient support apparatus 30 when the fowler section 40 is lowered.

Advantages of these various embodiments include, for example, easy and ergonomic access to the patient handles 92, 104, 116 which allows the patient to readjust the patient's position on the patient support deck 38 after the patient has slipped or is in an otherwise uncomfortable position, without the assistance of a caregiver. Moreover, bed pendants (corded bed control devices) are attached to the fowler section 40 and move with the patient when the fowler section 40 is articulated relative to the support frame 36 and/or another section. When the headboard assembly 60 moves with the fowler section 40, the cord of the bed pendant does not get stretched and the bed pendant can move with the patient. Additionally, the environment controls 84 allow the patient to adjust certain features, such as temperature, sound, and light, without the assistance of a caregiver. Finally, patients may be able to charge their electronic devices from charging ports on the headboard assembly 60. All of these features improve patient comfort.

It will be appreciated that all or any combination of the features described in the above embodiments may be incorporated within a single headboard assembly 60.

It will be further appreciated that the terms "include," "includes," and "including" have the same meaning as the terms "comprise," "comprises," and "comprising."

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A patient support apparatus comprising:
a support structure including a base and a support frame;
a patient support deck operatively attached to the support frame and having a plurality of deck sections including a fowler section arranged for movement relative to the support frame; and
a headboard assembly including:
a headboard body operatively attached to the fowler section for concurrent movement with the fowler section relative to the support frame,
a modular headboard section,
a mounting bracket coupled to the fowler section,
an articulating arm operatively attached to the mounting bracket at a first end and supporting the modular headboard section at a second end for movement relative to the headboard body between a plurality of configurations including a first configuration and a second configuration different from the first configuration, and
a receiver shaped to receive the modular headboard section in a third configuration to at least partially limit movement of the modular headboard section relative to the receiver in one or more degrees of freedom.

2. The patient support apparatus of claim 1, wherein the modular headboard section is arranged to present a work surface for use by a caregiver in the first configuration; and wherein the modular headboard section is arranged to present the work surface for use by a patient in the second configuration.

3. The patient support apparatus of claim 2, wherein movement of the modular headboard section from the first configuration towards the second configuration pivots the work surface by approximately 90 degrees.

4. The patient support apparatus of claim 2, wherein the work surface is arranged facing away from the base in the first configuration.

5. The patient support apparatus of claim 4, wherein the work surface is arranged facing towards the headboard body in the second configuration.

6. The patient support apparatus of claim 1, wherein the modular headboard section is arranged for movement to a stowed position disposed adjacent to the headboard body.

7. The patient support apparatus of claim 1, wherein the modular headboard section includes a handle arranged to be grasped by a patient during operation in the third configuration to facilitate patient egress.

8. The patient support apparatus of claim 1, wherein the headboard assembly further includes a first joint interposed between the mounting bracket and the articulating arm to permit pivoting movement of the articulating arm relative to the fowler section between the plurality of configurations.

9. The patient support apparatus of claim 8, wherein the first joint is a ball and socket joint.

10. The patient support apparatus of claim 8, wherein the headboard assembly further includes a second joint interposed between the modular headboard section and the articulating arm to permit pivoting movement of the modular headboard section relative to the articulating arm between the plurality of configurations.

11. The patient support apparatus of claim 10, wherein the second joint is a ball and socket joint.

12. The patient support apparatus of claim 10, wherein the articulating arm includes a third joint arranged between the first joint and the second joint to permit movement of the first joint relative to the second joint.

13. The patient support apparatus of claim 1, further comprising a clip coupled to the modular headboard section for holding items.

14. The patient support apparatus of claim 13, wherein the clip includes a biased clamp pivotally mounted to the modular headboard section.

15. The patient support apparatus of claim 1, wherein the receiver comprises a pocket sized for slidably receiving a bottom portion of the modular headboard section to limit lateral movement of the modular headboard section.

16. The patient support apparatus of claim 1, further comprising a pair of head end side rails operatively attached to the support structure, with one of the pair of head end side rails defining the receiver.

17. The patient support apparatus of claim 16, wherein the modular headboard section is arranged laterally between the pair of head end side rails in the first configuration.

18. The patient support apparatus of claim 17, wherein the modular headboard section is arranged laterally between the pair of head end side rails in the second configuration.

19. A patient support apparatus comprising:
a support structure including a base and a support frame;
a patient support deck operatively attached to the support frame and having a plurality of deck sections including a fowler section arranged for movement relative to the support frame; and
a headboard assembly including:
- a headboard body operatively attached to the fowler section for concurrent movement with the fowler section relative to the support frame,
- a modular headboard section, and
- an articulating arm coupled to the support frame and supporting the modular headboard section for movement relative to the headboard body between a plurality of configurations including a first configuration and a second configuration different from the first configuration; and
- a pair of head end side rails operatively attached to the support structure, at least one of the pair of head end side rails defining a receiver shaped to receive the modular headboard section in a third configuration to at least partially limit movement of the modular headboard section relative to the receiver in one or more degrees of freedom.

\* \* \* \* \*